(12) United States Patent
Chavez et al.

(10) Patent No.: US 12,403,303 B2
(45) Date of Patent: Sep. 2, 2025

(54) LEAD FIXATION DEVICES FOR SECURING A LEAD TO A CRANIUM

(71) Applicant: NeuroPace, Inc., Mountain View, CA (US)

(72) Inventors: Alfonso Chavez, San Jose, CA (US); David A. Greene, Fort Wayne, IN (US)

(73) Assignee: NeuroPace, Inc., Mountain View, CA (US)

( * ) Notice: Subject to any disclaimer, the term of this patent is extended or adjusted under 35 U.S.C. 154(b) by 308 days.

(21) Appl. No.: 18/077,668

(22) Filed: Dec. 8, 2022

(65) Prior Publication Data

US 2023/0104746 A1    Apr. 6, 2023

Related U.S. Application Data

(62) Division of application No. 16/692,964, filed on Nov. 22, 2019, now Pat. No. 11,547,850.

(60) Provisional application No. 62/773,121, filed on Nov. 29, 2018.

(51) Int. Cl.
   *A61N 1/00*    (2006.01)
   *A61N 1/05*    (2006.01)

(52) U.S. Cl.
   CPC ................... *A61N 1/0539* (2013.01)

(58) Field of Classification Search
   None
   See application file for complete search history.

(56) References Cited

U.S. PATENT DOCUMENTS

| 4,328,813 A | 5/1982 | Ray |
| 5,464,446 A | 11/1995 | Dreesen et al. |
| 5,843,150 A | 12/1998 | Dressen et al. |

(Continued)

FOREIGN PATENT DOCUMENTS

| WO | 2001176498 A2 | 10/2001 |
| WO | 2004103468 A1 | 12/2014 |

OTHER PUBLICATIONS

Biomet Microfixation. Neuroimplant System. Product Brochure, 8 pgs. (2013).

(Continued)

*Primary Examiner* — John R Downey
*Assistant Examiner* — Anant A Gupta
(74) *Attorney, Agent, or Firm* — LOZA & LOZA, LLP; David S. Sarisky

(57) ABSTRACT

A lead fixation device for securing a first portion of a lead relative to a hole formed through a skull includes a skull attachment member having an upper surface and a lower surface and a bore extending through and between the upper surface and the lower surface. The lead fixation device also includes a lead compression mechanism integral with the skull attachment member and aligned with the bore of the skull attachment member. The lead compression mechanism defines a passageway through the lead fixation device, which passageway is characterized by a diameter that is defined by the lead compression mechanism. The lead compression mechanism is configured to transition the diameter from a first size to a second size greater than the first size upon insertion of an implant tool through the passageway, and from the second size to the first size upon removal of the implant tool from the passageway.

9 Claims, 14 Drawing Sheets

(56) References Cited

U.S. PATENT DOCUMENTS

| | | | |
|---|---|---|---|
| 5,865,842 A * | 2/1999 | Knuth | A61B 5/24 |
| | | | 607/116 |
| 5,865,843 A | 2/1999 | Baudino | |
| 5,927,277 A | 7/1999 | Baudino et al. | |
| 6,044,304 A | 3/2000 | Baudino | |
| 6,134,477 A | 10/2000 | Knuteson et al. | |
| 6,210,417 B1 | 4/2001 | Baudino et al. | |
| 6,319,241 B1 | 11/2001 | King et al. | |
| 6,321,104 B1 | 11/2001 | Gielen et al. | |
| 6,356,792 B1 | 3/2002 | Errico et al. | |
| 6,795,737 B2 | 9/2004 | Gielen et al. | |
| 6,810,285 B2 | 10/2004 | Pless et al. | |
| 6,902,569 B2 | 6/2005 | Parmer et al. | |
| 7,204,840 B2 | 4/2007 | Skakoon et al. | |
| 7,235,084 B2 | 6/2007 | Skakoon et al. | |
| 7,580,756 B2 | 8/2009 | Schulte et al. | |
| 7,604,644 B2 | 10/2009 | Schulte et al. | |
| 7,636,596 B2 | 12/2009 | Solar | |
| 7,637,915 B2 | 12/2009 | Parmer et al. | |
| 7,660,621 B2 | 2/2010 | Skakoon et al. | |
| 7,704,260 B2 | 4/2010 | Skakoon et al. | |
| 7,744,606 B2 | 6/2010 | Miller et al. | |
| 7,766,394 B2 | 8/2010 | Sage et al. | |
| 7,766,922 B1 | 8/2010 | Daglow et al. | |
| 7,815,651 B2 | 10/2010 | Skakoon et al. | |
| 7,828,809 B2 | 11/2010 | Skakoon et al. | |
| 7,833,231 B2 | 11/2010 | Skakoon et al. | |
| 7,857,820 B2 | 12/2010 | Skakoon et al. | |
| 7,949,410 B2 | 5/2011 | Rodriguez | |
| 7,976,530 B2 | 7/2011 | Johnson et al. | |
| 7,988,674 B2 | 8/2011 | Adams et al. | |
| 8,116,850 B2 | 2/2012 | Solar | |
| 8,152,792 B1 | 4/2012 | Kornel | |
| 8,192,445 B2 | 6/2012 | Parmer et al. | |
| 8,845,656 B2 | 9/2014 | Skakoon et al. | |
| 8,911,452 B2 | 12/2014 | Skakoon et al. | |
| 9,457,180 B2 | 10/2016 | Bucholz | |
| 9,545,509 B2 | 1/2017 | Greene | |
| 9,572,973 B2 | 2/2017 | Chavez et al. | |
| 2005/0015128 A1 | 1/2005 | Rezai et al. | |
| 2005/0182421 A1 | 8/2005 | Schulte et al. | |
| 2005/0182422 A1 | 8/2005 | Schulte et al. | |
| 2005/0182424 A1 | 8/2005 | Schulte et al. | |
| 2005/0182425 A1 | 8/2005 | Schulte et al. | |
| 2009/0112327 A1 | 4/2009 | Lane et al. | |
| 2009/0306750 A1 | 12/2009 | Boling et al. | |
| 2009/0326610 A1 | 12/2009 | Pless et al. | |
| 2010/0179563 A1 | 7/2010 | Skakoon et al. | |
| 2010/0312193 A1 | 12/2010 | Stratton | |
| 2011/0270187 A1 | 11/2011 | Nelson | |
| 2012/0245529 A1 | 9/2012 | Hummen et al. | |
| 2013/0066410 A1 | 3/2013 | Funderburk | |
| 2013/0304216 A1 | 11/2013 | Papsa et al. | |

OTHER PUBLICATIONS

Aesculap Inc. Cranial Fixation Systems. Product Brochure, 11 pgs. (2014).

Miller et al. "Stereotactic bony trajectory preservation for responsive neurostimulator lead placement following depth EEG recording." Cureus 8(3):3549. DOI 10.7759/cureus.549, 6 pgs. (Mar. 30, 2016).

Synthes CMF. "MatrixNEURO. The next generation cranial plating system." Product Brochure, 10 pgs. (2006).

* cited by examiner

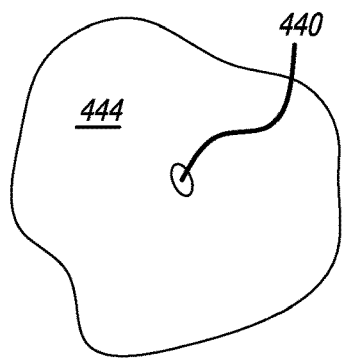
*FIG. 10A*
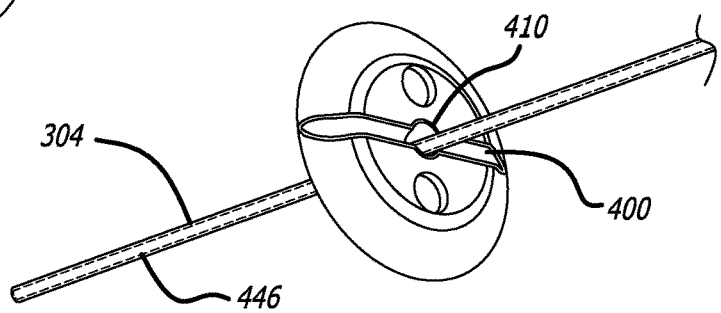
*FIG. 10B*
*FIG. 10C*
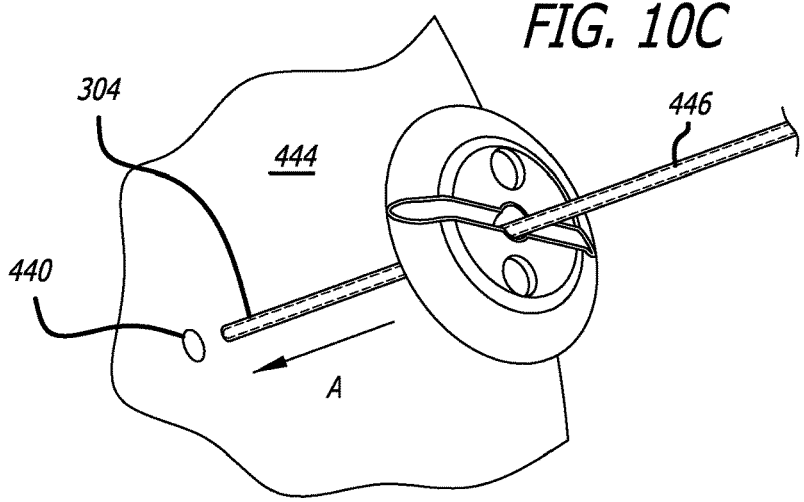
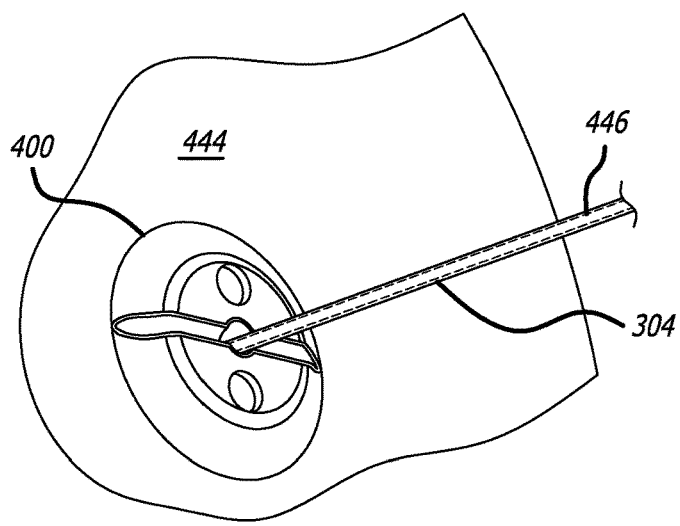
*FIG. 10D*

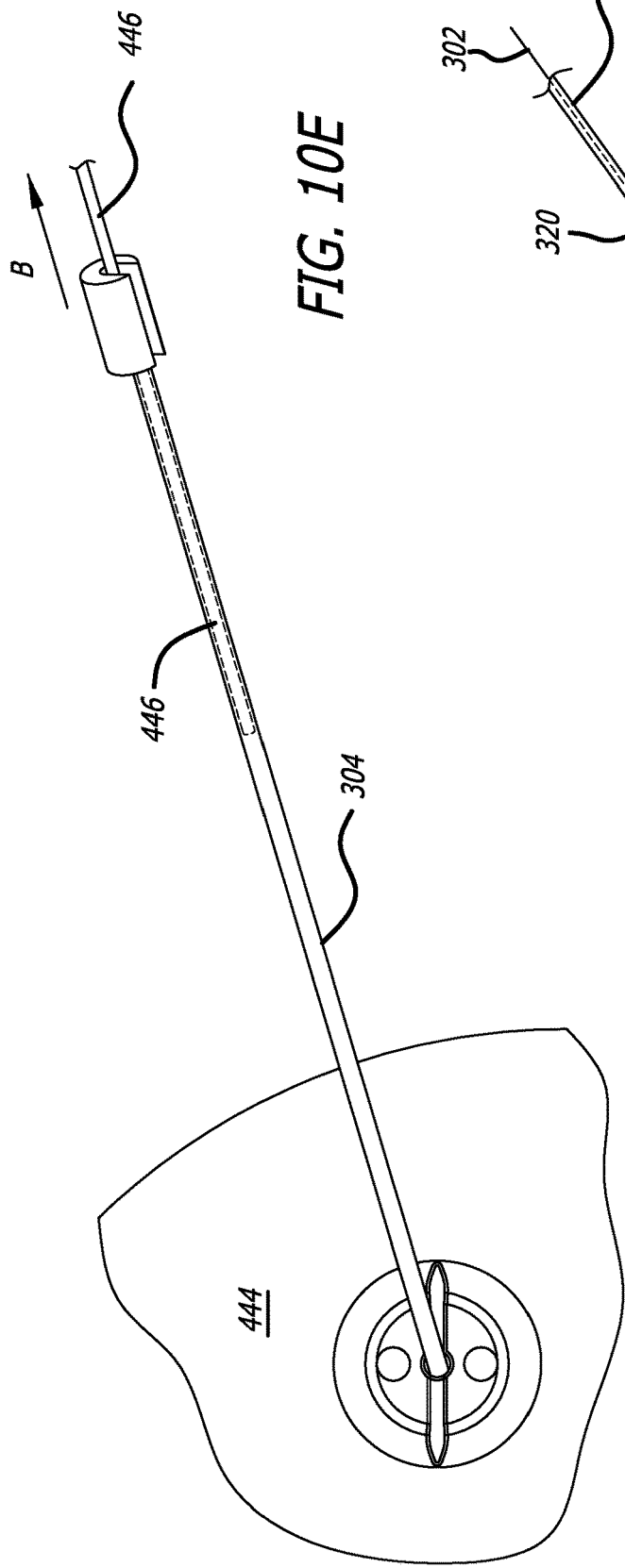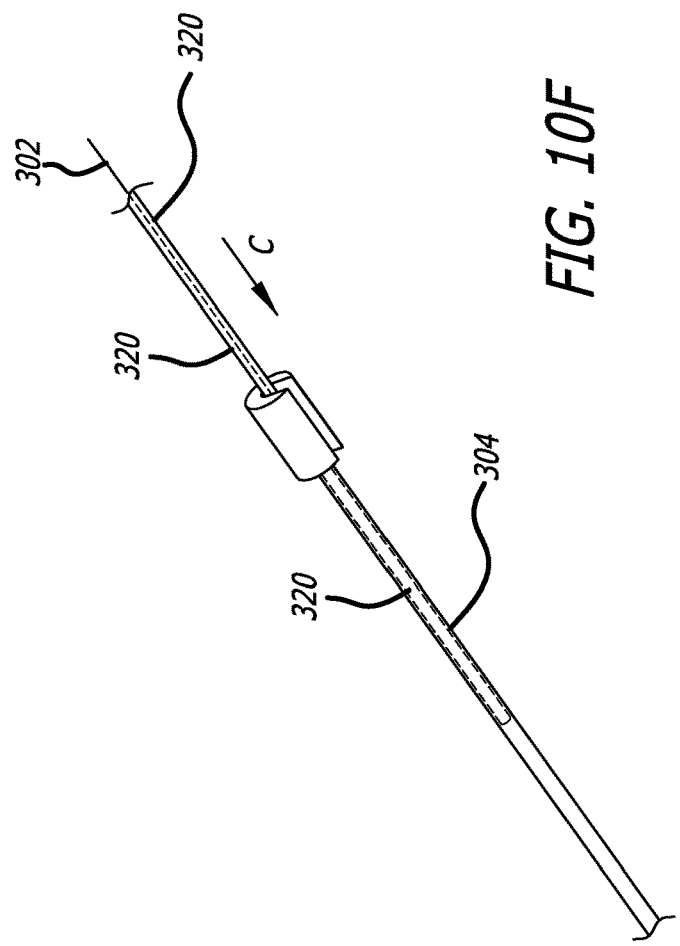

LEAD FIXATION DEVICES FOR SECURING A LEAD TO A CRANIUM

CROSS-REFERENCE TO RELATED APPLICATIONS

This application is a divisional of U.S. application Ser. No. 16/692,964, filed on Nov. 22, 2019, now U.S. Pat. No. 11,547,850, entitled "Lead Fixation Devices for Securing a Lead to a Cranium," which claims the benefit of and priority to U.S. Provisional Patent Application Ser. No. 62/773,121, filed Nov. 29, 2018, for "Lead Fixation Devices for Securing a Lead to a Cranium," the entire disclosures of which are incorporated herein by reference.

TECHNICAL FIELD

The present disclosure relates generally to apparatuses and methods used when implanting a medical device in a patient, and more particularly, to lead fixation devices for securing a lead to a cranium and methods for using the same.

BACKGROUND

Some diagnostic or interventional medical procedures require implanting one or more leads through a hole in a patient's cranium. Once the surgeon places a lead so that the distal end is at a desired location, the surgeon wants the lead to stay there for whatever ultimate medical purpose the lead has, for example, to monitor physiological parameters from a patient or to deliver a therapy to the patient. Usually, however, there are steps subsequent to placing the lead that are necessary to complete the surgical procedure, and some of these may cause inadvertent displacement of the lead away from the desired location, which may not be corrected easily or efficiently.

Generally, leads may be provided with electrodes configured to sense information from the brain or to deliver a form of stimulation to the brain intended to modulate neural activity, such as electrical stimulation. The sensing and/or stimulation may occur at a distal end of the lead, for example, through electrodes exposed to brain tissue at a distal end, wherein the signals are communicated through conductors disposed in the lead body extending to a lead proximal end. Connections available at the lead proximal end allow the lead to be connected to another medical device, implanted or external, that processes the sensed signals and/or generates the form of stimulation.

For example, in the responsive neurostimulation system manufactured under the tradename RNS SYSTEM by NeuroPace, Inc., the proximal ends of one or more implanted brain leads can be connected to another implanted medical device, namely a neurostimulator that is seated in a tray or ferrule in a craniectomy in the patient's skull. In another example, the leads may be implanted in a patient so that an intracranial monitoring procedure can be undertaken for a period (e.g., several days or a couple of weeks), with the proximal ends of the implanted leads being connected to external equipment monitoring the patient's brain activity, such as to identify a focus or the foci of epileptiform activity in the patient.

There are multiple types of brain leads currently available. In applications where the leads are being used to sense or stimulate brain tissue at or near the focus of undesirable epileptiform activity, there is a depth lead (also sometimes referred to as a "deep brain lead" or as a "stereotactic depth lead", because this lead type is often implanted using stereotaxy, a three-dimensional localization and placement procedure) and a cortical strip lead (also known simply as a "cortical lead" or as a "subdural lead", because this lead type is usually implanted underneath the dura mater).

A depth lead is implanted so that the distal end is located in the brain tissue, in or adjacent a structure that is deemed to be associated with the generation of the undesirable activity. A cortical strip lead is implanted so that the distal end lays on a surface of the brain at or adjacent brain tissue that is believed to comprise an epileptic focus. The intended location of the distal end of the brain lead in or on the brain is referred to hereinafter as the "target".

A lead manufacturer may make different lead types in one or more standard lengths, rather than in lengths customized for a particular application in a particular patient. In addition, the depth lead type may be intended to be implanted using stereotactic equipment or some other tool that requires some length in excess of that which is needed to extend from the cranium and the connection to another medical device and the target (e.g., so that the lead is long enough to extend through the distance required when using a stereotactic frame mounted to the patient). For at least the reason that a lead may be manufactured to have more length than is necessary to traverse the distance between the proximal connection to another implant or external equipment and the target, brain leads are often manufactured to be quite flexible. That is, if the lead is flexible, excess length can be coiled or folded at the surface of the skull before the scalp is replaced. Further, flexibility may be considered a better alternative than a stiff lead when the lead is to remain in place in or on a surface of the brain chronically, as opposed to acutely, such as to minimize tissue damage and to optimize the integrity or resolution of signals. Brain leads manufactured and sold with the RNS SYSTEM, for example, have a flexibility on par with that of a piece of cooked spaghetti.

When implanting a lead in the brain tissue, though, its relative flexibility can present challenges when delivering the distal end to the target. Accordingly, a brain lead is often provided with an inner lumen through which a removable stiffener, such as a stylet, can be disposed. The stylet lends stability to the lead while the distal end is routed to the target, and is then removed when the lead has been positioned where it is intended to remain, either acutely or chronically. It is undesirable, however, if the act of withdrawing the stylet causes the distal end to move away from the target.

Equipment or tools used in implanting a brain lead can also unintentionally cause the distal end of a brain lead to move away from the target in procedural steps undertaken subsequent to placing the lead. For example, a slotted cannula is often employed in implanting leads stereotactically, in which a hole is formed in the patient's skull at a location calculated to allow an appropriate trajectory of a lead to a deep brain target. In one example of such a procedure, a frame is attached to the patient, and a guide tube is oriented to achieve the desired trajectory relative to the skull hole. A cannula is inserted through the guide tube, such that its range of motion is constrained by the guide tube. The cannula may be provided with a removable rod disposed in an inner lumen thereof. The cannula is advanced through the skull hole towards the target. The inner rod in the cannula prevents tissue from backing up into the cannula while it is advanced.

When the cannula has been advanced to or approximate the target, the inner rod is removed and a depth lead inserted into the cannula lumen. The surgeon then advances the depth lead to the target. (Sometimes the depth lead is marked in advance at a proximal location, for example, with a stop gauge, to provide feedback to the surgeon when the target has been reached.) Once the distal end of the lead reaches the target, the cannula must be withdrawn from the brain and the lead must be extracted from the cannula, so the stereotactic equipment can be removed. A cannula is often provided with a longitudinally-extending slot with a width wide enough to accommodate the diameter of the lead body for this purpose, i.e., so that the lead can be stripped away from the cannula using the slot, rather than having to retract the cannula over the lead body. This allows the lead to be manufactured with somewhat less excess lead length than if the lead had to be long enough to retract the cannula over the very proximal end of the lead. As is the case with withdrawing a stylet, it is undesirable if the act of disengaging the lead body from a cannula (or other apparatus used for stereotaxy) causes the distal end of the brain lead to move away from the target.

SUMMARY

The present disclosure relates to a lead fixation device for securing a first portion of a lead relative to a hole formed through a skull. The lead fixation device includes a skull attachment member having an upper surface and a lower surface and a bore extending through and between the upper surface and the lower surface. The lead fixation device also includes a lead compression mechanism that is integral with the skull attachment member and aligned with the bore of the skull attachment member. The lead compression mechanism defines or forms a passageway through the lead fixation device, which passageway is characterized by a diameter that is defined by the lead compression mechanism. The lead compression mechanism is configured to transition the diameter from a first size to a second size greater than the first size upon insertion of an implant tool through the passageway, and from the second size to the first size upon removal of the implant tool from the passageway.

In one configuration, the compression mechanism is fixedly secure relative to the skull attachment member so that transition of the diameter between the first size and the second size results from radial outward compression of the compression mechanism and radial inward expansion of the compression mechanism relative to an axis through the passageway. The first portion of the lead has a diameter and the first size of the diameter of the compression mechanism is less than the diameter of the lead to thereby secure the first portion of the lead in place at the skull hole.

The present disclosure also relates to a lead fixation device for securing a portion of a lead relative to a surface of a skull. The lead fixation device includes a skull attachment member having an upper surface and a lower surface. The lead fixation device also includes a lead compression mechanism that is integral with the skull attachment member. The lead compression mechanism is formed of a flexible material while the skull attachment member is formed of a material more rigid than the lead compression mechanism. The lead compression mechanism forms a passageway through the skull attachment member. In one embodiment, the passageway is characterized by a slot that faces in the direction of the lower surface and extends along the length of the passageway. In another embodiment, the passageway is characterized by a slot that faces in the direction of the upper surface and extends along the length of the passageway.

The lead compression mechanism is formed of a flexible material and is configured to transition a width of the slot from an initial size that is less than the diameter of the portion of the lead, to an expanded size that is greater than the initial size upon receipt of appropriately directed first forces in a region of the lead compression mechanism that forms the passageway. Such first forces increase the width and allow for the portion of the lead to slide into the passageway. The lead compression mechanism is further configured to transition the width of the slot from the initial size to a collapsed size upon receipt of appropriately directed second force in a region of the lead compression mechanism that forms the passageway. Such second forces decrease the width and secure the portion of the lead inside the passageway.

BRIEF DESCRIPTION OF THE DRAWINGS

Various aspects of apparatuses and methods will now be presented in the detailed description by way of example, and not by way of limitation, with reference to the accompanying drawings, wherein:

FIG. 10A-10J are illustrations of a lead implant procedure using the lead fixation device of FIGS. 4A-4D.

DETAILED DESCRIPTION

Disclosed herein is a lead fixation device that allows the body of a brain lead to be secured relative to a hole formed through the skull and at the surface of a patient's skull while a stiffening element, such as a stylet, remains in place in a lumen of the lead body. The stiffening element thus can be withdrawn from the lead after the lead fixation accessory is in place, reducing the likelihood that the act of pulling out the stylet will displace the distal end of the implanted lead away from the target. Also disclosed herein are embodiments of lead fixation device that allow the body of a brain lead to be secured at or along a surface of a skull at a location between the point where the lead body exits the skull and the point where the lead connects to an implanted medical device.

The embodiments are described primarily with reference to the lead being an electrode-bearing lead, as might be used in an application for deep brain stimulation or direct brain stimulation such as the responsive stimulations applications by NeuroPace, Inc. of Mountain View, CA. It should be appreciated, however, that the lead fixation devices may be used with good results to secure a segment of a different type of medical device, such as a catheter or other medical instrument (with a diameter compatible with the accessory), relative to a surface of the skull prior to and/or during use of the medical device in its intended application.

Overview of Procedures to Implant Brain Leads

For purposes of illustration, procedures to implant a depth lead and a cortical strip lead will be described with reference to a responsive neurostimulation system, in which a surgeon commonly uses both lead types.

Figure 1A:
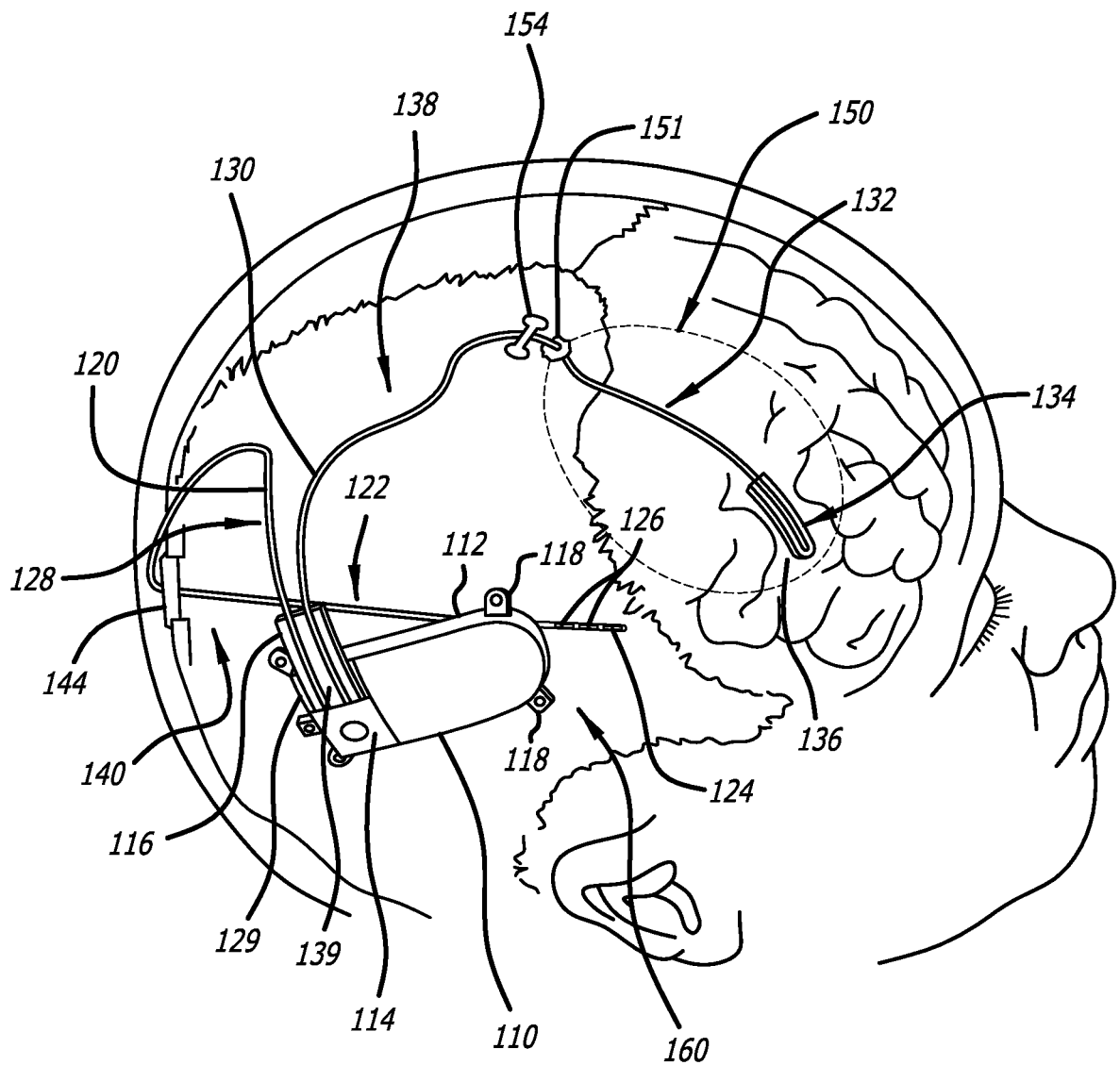
FIG. 1A is a schematic of a patient's cranium showing implanted components of a neurostimulation system, including leads and a neurostimulator, and related surgical accessories, including a burr hole cover and a lead fixation plate.

With reference to FIG. 1A, a neurostimulator 110 and leads 120, 130 of a responsive neurostimulation system are shown schematically, implanted in a patient. To implant a lead, the surgeon needs access to the brain. A surgeon may gain access to the brain for purposes of implanting a lead by creating an opening through the skull. A opening may be created by drilling a hole through the skull, by performing a craniotomy (temporarily removing a bone flap from the skull and replacing the flap after access to the brain is no longer needed) or by performing a craniectomy (permanently removing a bone flap from the skull). Such opening may be used exclusively for lead implant purposes, or may be used for another/additional purpose (for example, the surgeon can first deliver a lead to a target through an opening formed as part of a craniectomy, then use the same opening to implant another medical device, such as a neurostimulator). The term "skull hole" is used herein to refer to any category of opening formed in a patient's skull to gain access to the subdural spaces and to the brain.

In FIG. 1A, three skull holes have been formed: a burr hole 140 for purposes of implanting a depth lead 120, a craniotomy 150 for purposes of implanting a cortical strip lead 130, and a craniectomy 160 in which a ferrule or tray 112 and a neurostimulator 110 are ultimately implanted. More particularly, the surgeon may use an air-powered drill to form an annular burr hole 140 of a diameter between 5-30 mm, with 14 mm being a commonly-used diameter, for purposes of implanting a depth lead 120. Using appropriate tools, the surgeon may also perform a craniotomy 150 for purposes of implanting a cortical strip lead 130, and additionally a craniectomy 160 in which to ultimately situate a neurostimulator at the patient's skull.

In FIG. 1A, a distal portion 122 of the depth lead 120 extends into the patient's brain tissue from a 14-mm burr hole 140, and a proximal portion 128 extends proximally from the burr hole where it is plugged in at a proximal end 129 to a connector 114 of an implanted neurostimulator 110. A distal portion 132 of a cortical strip lead 130 extends from a fissure like hole or opening 151 at an edge of the craniotomy 150 onto a surface of the patient's brain, between the brain and the dura mater (not shown), and a proximal portion 138 extends proximally from the hole where it is plugged in at a proximal end 139 to the connector 114. The neurostimulator 110 has a strain relief 116 in the location where the proximal ends 129, 139 of the leads connect, to discourage the leads from unintentional disconnection.

A distal end 124 of the depth lead 120 includes a plurality of electrodes 126 (three are shown in FIG. 1A), that can be used either for sensing electrographic activity from the brain or for delivering a therapy of electrical stimulation to it in an effort to modulate neural activity (e.g., lessen the severity of a seizure). Conductors extending the length of the lead body (not shown) and connected at the connector 114 to the neurostimulator 110 allow the neurostimulator to process the sensed signals and to generate the stimulation signals. A distal end 134 of the cortical strip lead 130 ends in a paddle 136 that, on a brain-facing surface thereof (not shown in FIG. 1A), exposes another plurality of electrodes (e.g., four) to the brain surface underneath the dura mater. These electrodes are also in electrical communication with the neurostimulator 110 via conductors in the cortical strip lead 130 and the connection at the connector 114.

In addition to the burr hole 140 or the craniotomy 150 opening 151, a lead, especially of the cortical strip lead type, may be implanted using another opening in the cranium. More specifically, to implant the neurostimulator 110, the surgeon cuts a craniectomy 160 hole using a template that approximates the shape of the neurostimulator. The surgeon fits a tray or "ferrule" 112 into the hole and attaches or otherwise secures it to the cranium, for example, using bone screws and/or folding tabs 118 providing on the tray. The surgeon then situates the neurostimulator 110 into the tray 112. However, before placing the tray 112, the surgeon can use the craniectomy 160 hole to implant a cortical strip lead, such as the cortical strip lead 130, and then connect the proximal end thereof to the neurostimulator connector. (FIG. 1A does not show any lead implanted using the craniectomy 160 in which the tray 112 and neurostimulator 110 are situated.)

Figure 1B:
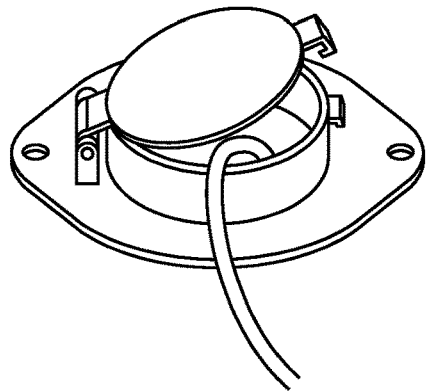
FIGS. 1B and 1C are illustrations of known burr hole covers.
Figure 1C:
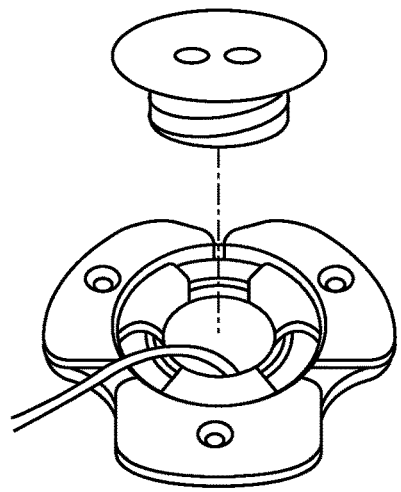

Both of the implanted leads 120, 130 in FIG. 1A are shown secured with known lead fixation accessories. The depth lead 120 implanted through the burr hole 140 is shown secured with a burr hole cover 144 which substantially fills the 14-mm diameter burr hole except for an aperture therethrough that permits passage of the lead body. Examples of lead fixation accessories designed for burr holes are illustrated in FIGS. 1B and 1C.

Some burr hole lead fixation devices are designed for use with mechanical parts that need to be actuated in order to achieve fixation of the lead body, and others rely on friction fit or compression to limit movement of the lead relative to the device. Some require at least one element of the accessory to be put in place before a procedure to implant a lead is begun. Some allow fixation only after any stiffening element used in implanting the lead has been removed. With reference to FIG. 1B, a burr hole lead fixation accessory manufactured by Medtronic, Inc. under the tradename "STIMLOC" uses several interlocking parts to secure a lead body. With reference to FIG. 1C, a two-piece burr hole cover manufactured by NeuroPace, Inc. relies in part on fitting a portion of the lead body into a groove in base element to reduce the likelihood that further manipulation of the lead portion extending proximally of the skull hole (e.g., to connect the lead to an implanted neurostimulator) will translate to movement of the distal end away from the target.

Figure 1D:
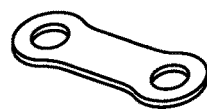
FIG. 1D is an illustration of a known lead fixation plate.

In FIG. 1A, the cortical strip lead 130 implanted through the craniotomy 150, and having a proximal portion 138 extending from the opening 151 at an edge of the craniotomy onto the surface of the skull is secured at a point on the lead body just proximal of where the lead body extends out of the hole, with a cranial plate 154. The cranial plate 154 is situated over the lead body and then secured to the surface of the skull on either side of the lead body with bone screws. Because of its shape, the type of cranial plate 154 shown in FIG. 1A is commonly referred to as a "dog bone". One such plate is shown in FIGS. 1D and 1s manufactured under the tradename "MATRIXNEURO" by Synthes CMF. The cranial plate 154 compresses the lead body to prevent lateral movement of the lead at the point of fixation to the skull. If the compression is inadvertently excessive (e.g., by overtightening of the screws or by a patient pressing down on the plate), the integrity of the lead may be compromised (e.g., the conductors between the electrodes at the lead distal end and the connector at the lead proximal end may be shorted).

The target for a depth lead 120 is usually more precise than the target for a cortical strip lead 130, at least in an application where the condition is epilepsy. That is, the target for a depth lead 120 is usually a particular structure in the brain, such as the subthalamic nucleus (STN) or the cingulate gyrus. The target for a cortical strip lead 130 may be somewhat more forgiving of imprecision, that is, the electrodes on the distal end 124 of the strip lead 130 may be destined to cover the general area on the surface of the brain where epileptic activity is believed to be focused. Thus, it may be especially beneficial to limit movement of the distal end of a depth lead once it has been placed at the target.

In part because of the need for precision and in part because the lead is being implanted into brain tissue as opposed to on a surface of it, a depth lead 120 is most often implanted using some form of stereotaxy (e.g., with a frame affixed to the patient's skull or a "frameless" version of it). Stereotactic procedures are well known and will not be described herein to any great degree. Briefly, however, one common method uses frame-based stereotaxis to approach a target or targets through a skull hole. The patient is given a local anesthetic and a rigid frame or fixation device is attached to the patient's head, and the brain is imaged (e.g., with a CT scan). The location of the target(s) is calculated based on a 'co-registration' of the images and the frame, fiducials or other registered points on the head. Then, the patient is sedated for surgery, the scalp is incised, and one or more skull holes are formed in the patient's cranium, each at a location that will allow an appropriate trajectory to the deep brain target(s).

A hole in the skull is often formed with some standard diameter, owing to the drills typically available in the operating room to create it. When an air drill is used to create a hole in the skull with a diameter of 5 mm or greater, the skull hole is often referred to as a "burr hole." Surgeons create standard-sized burr holes, because there are surgical accessories intended for use with burr holes that are intended for use with certain burr hole diameters, such as 14 mm. However, the diameter of a brain lead may be much smaller than that of a burr hole, because 14 mm is on the order of ten times greater than the diameter of the lead to be implanted. For example, some brain leads manufactured by NeuroPace, Inc. have a diameter of only 1.27 mm. Therefore, in some cases a surgeon may choose to use a smaller diameter hole through which to implant a lead. For example, a surgeon may choose to use a hand-held twist drill to create a hole with a diameter on the order of less than 5 mm (depending on the diameter of the twist drill bit: a common one results in a 3.2 mm diameter hole). A skull hole formed using a twist drill is sometimes referred to as a "twist drill hole".

Figure 2:
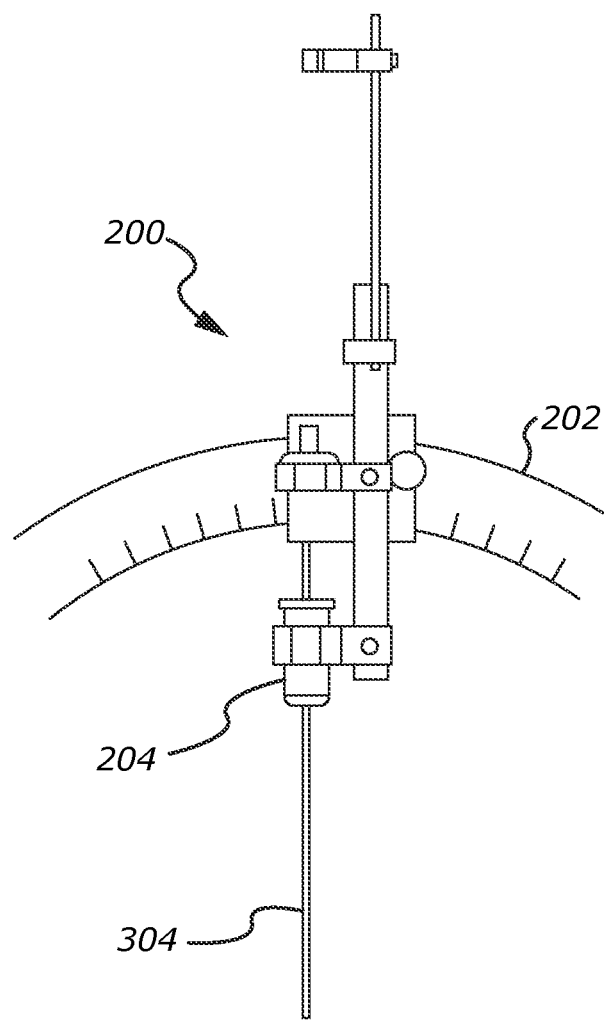
FIG. 2 is an illustration of some components of stereotactic equipment that may be used in a standard stereotactic procedure with a frame to implant a depth lead in a patient's brain.
Figure 3:
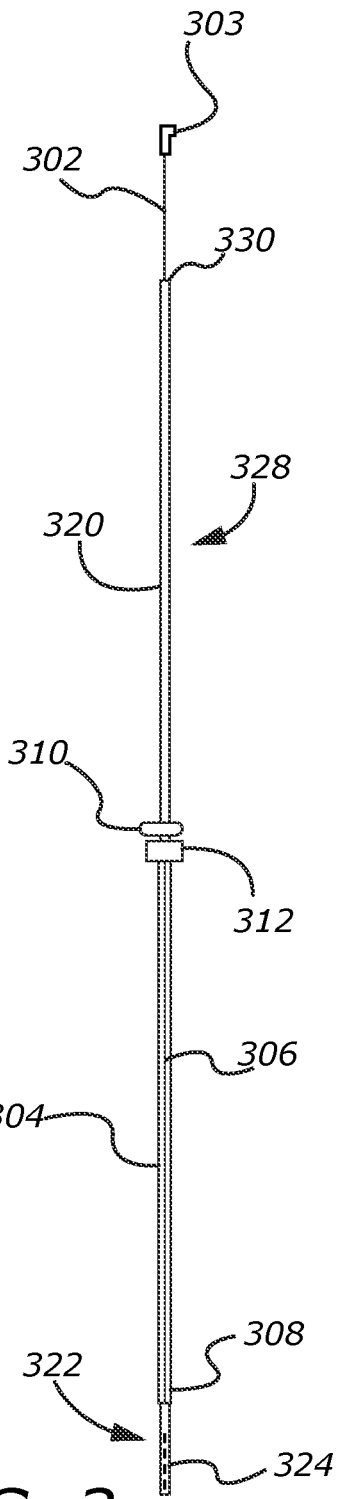
FIG. 3 is an illustration of a cannula (with a depth lead inserted therein) that may be used during a procedure for implanting a depth lead.
Figure 4A:
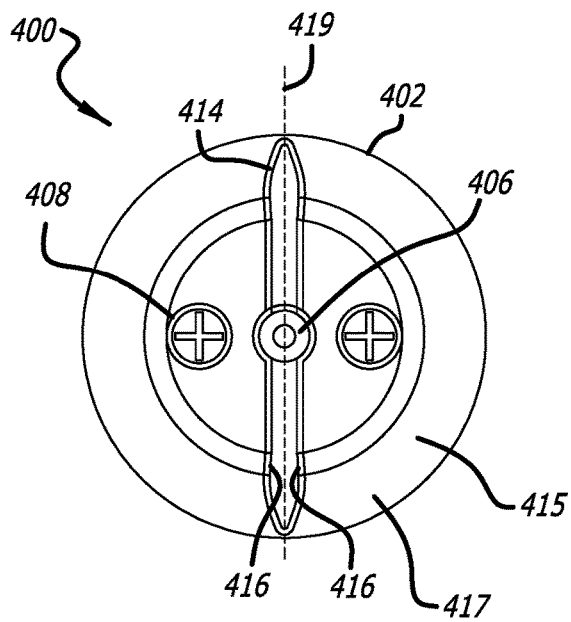
FIGS. 4A-4D are illustrations of a first embodiment of a lead fixation device for securing a lead at a hole in a skull and on a surface of the skull.
Figure 4B:
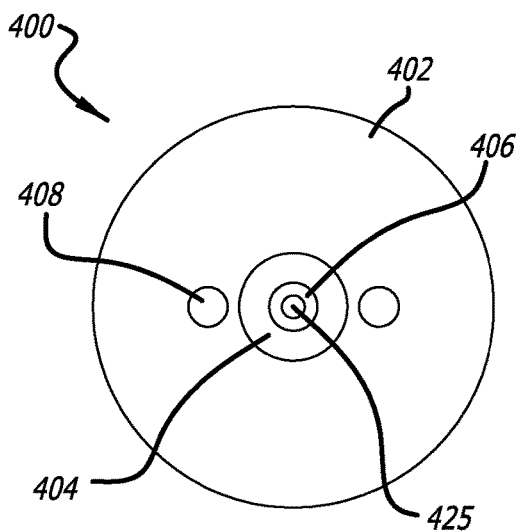
Figure 4C:
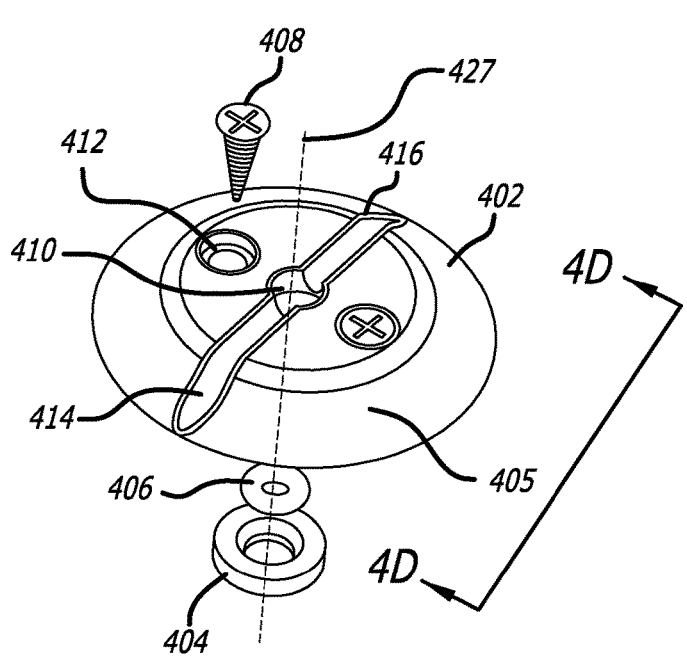
Figure 4D:
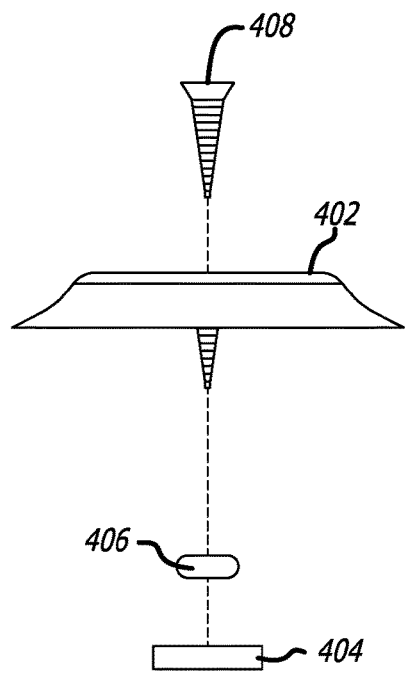
Figure 5A:
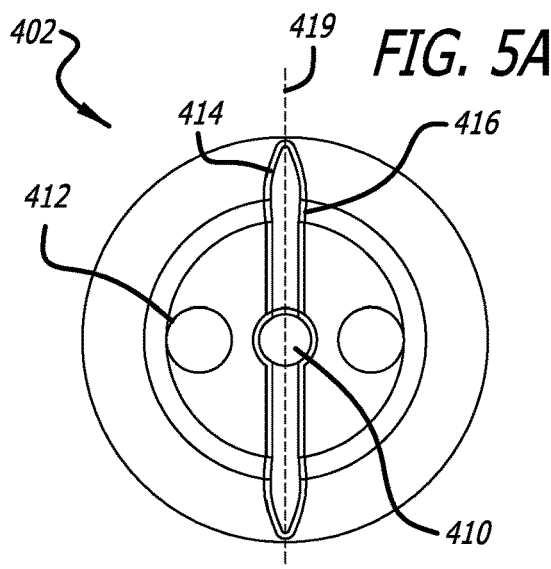
FIGS. 5A-5C are illustrations of a skull attachment member of the lead fixation device of FIGS. 4A-4D.
Figure 5B:
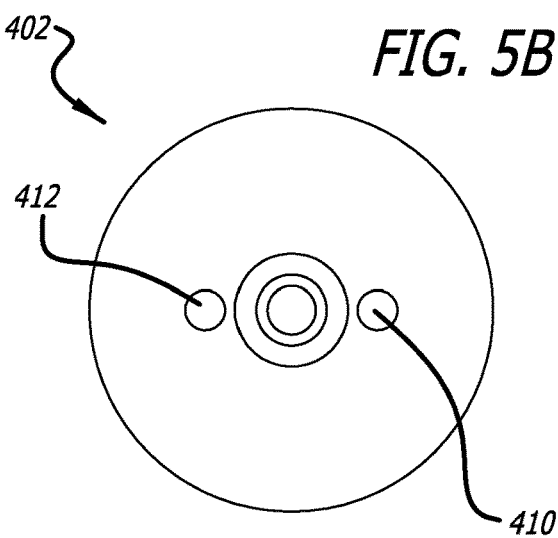
Figure 5C:
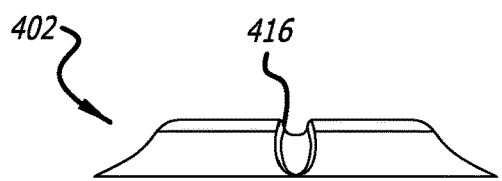
Figure 6:
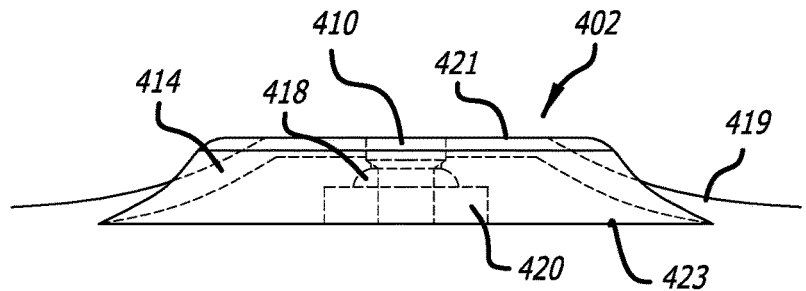
FIG. 6 is a side view drawing of the skull attachment member of FIG. 4A-4D.
Figure 7A:
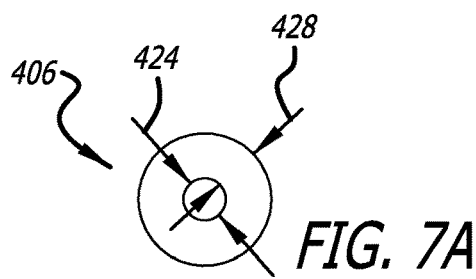
FIGS. 7A and 7B are illustrations of a compression mechanism of the lead fixation device of FIGS. 4A-4D.
Figure 8A:
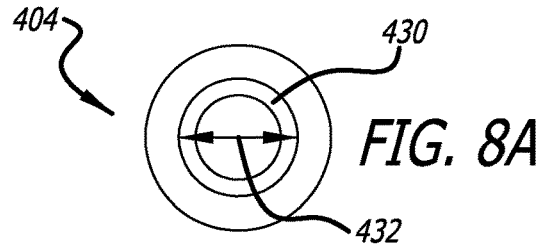
FIGS. 8A and 8B are illustrations of a locking member of the lead fixation device of FIGS. 4A-4D, that secures the compression mechanism in place in the skull attachment member.
Figure 7B:
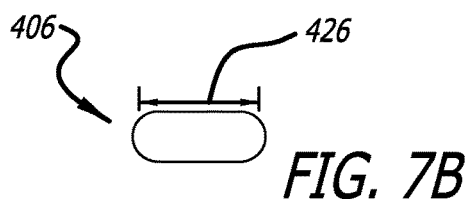
Figure 8B:
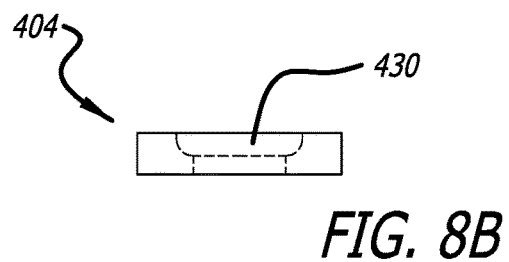
Figure 9A:
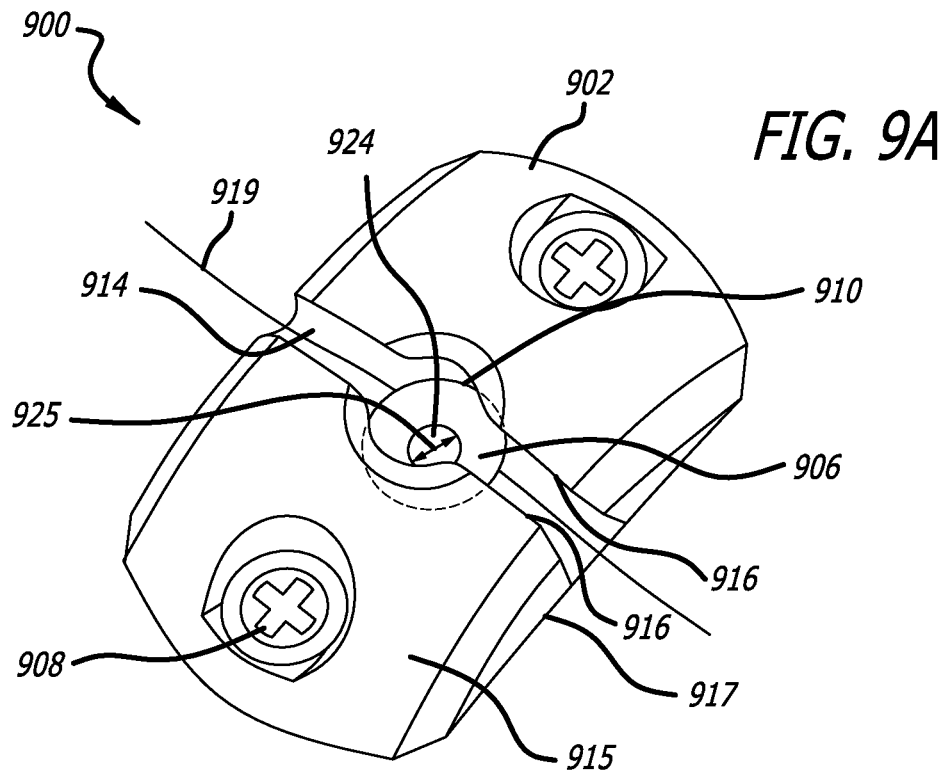
FIGS. 9A and 9B are illustrations of a second embodiment of a lead fixation device for securing a lead at a hole in a skull and on a surface of the skull.
Figure 9B:
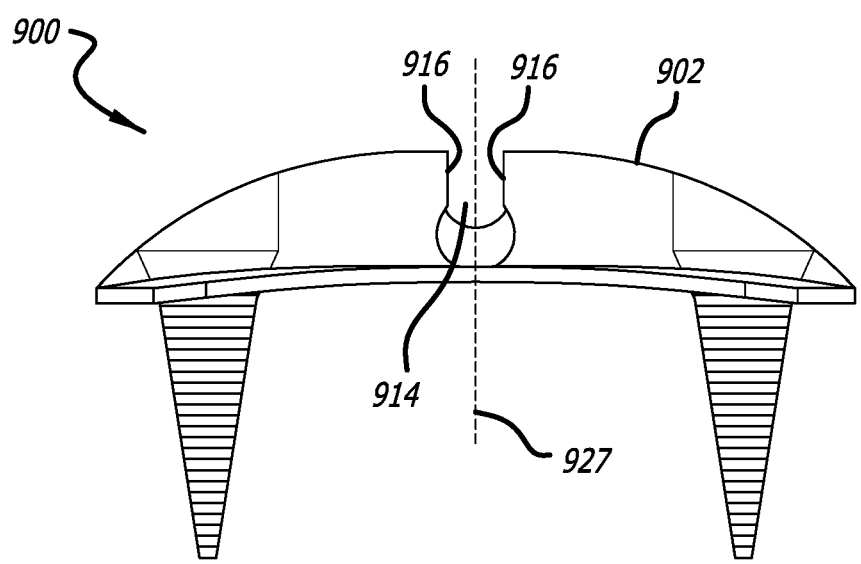
Figure 10G:
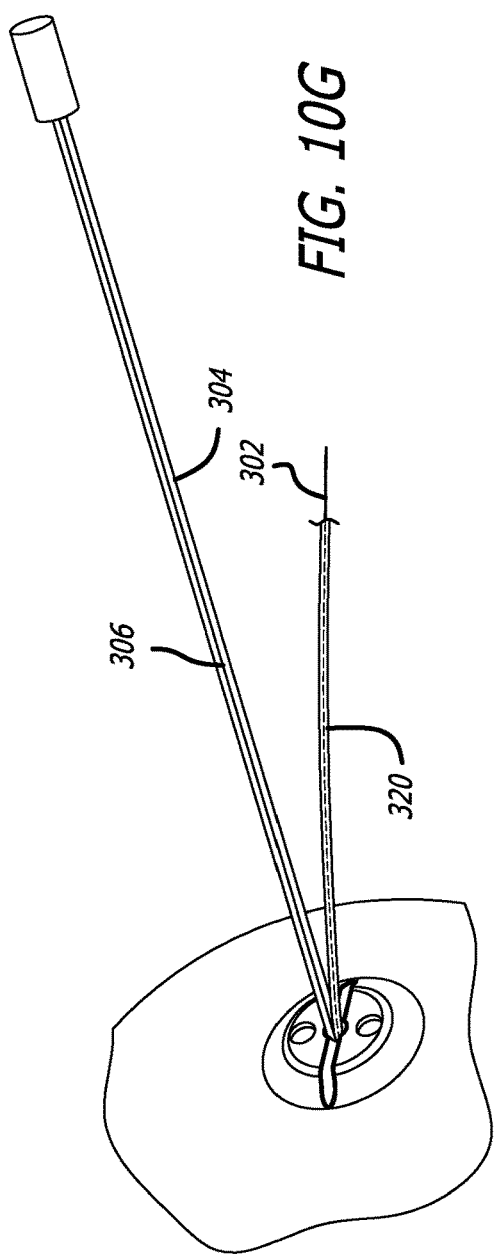
Figure 10H:
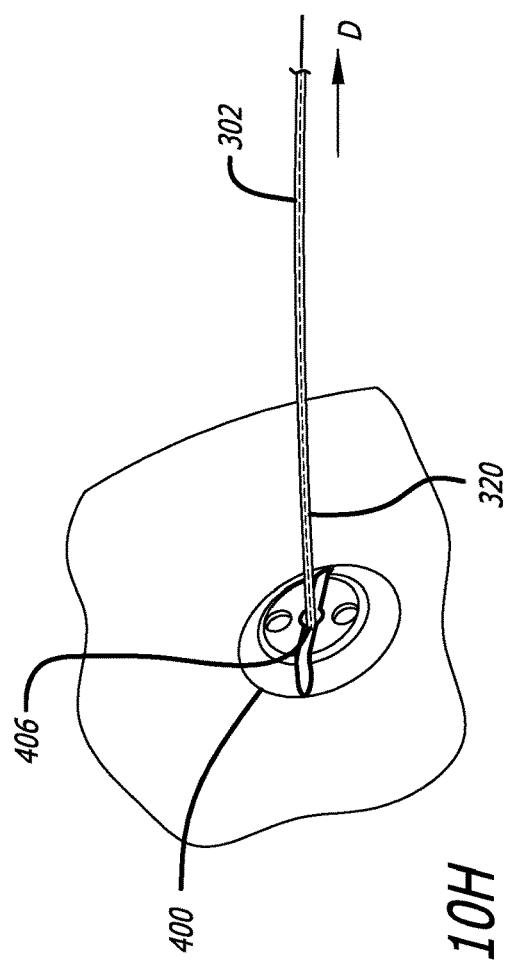
Figure 10I:
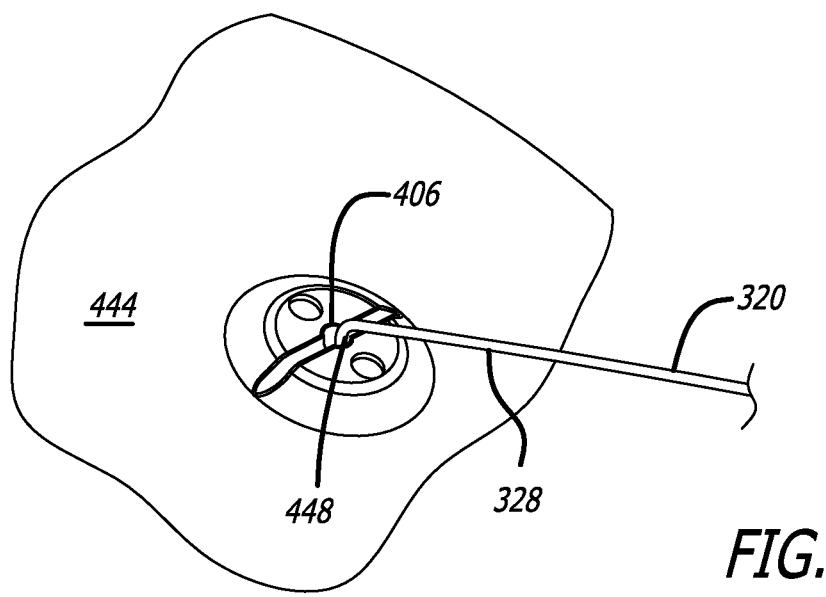
Figure 10J:
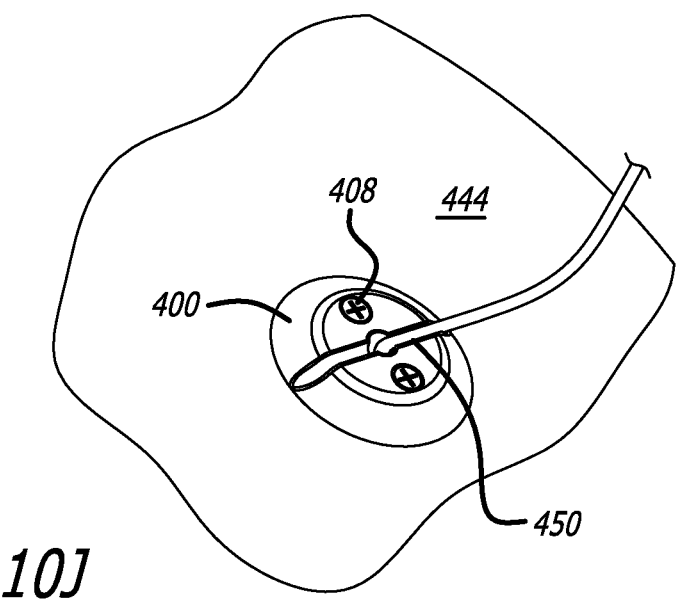

Referring now to FIGS. 2 and 3, part of the stereotactic equipment 200 is secured to the patient's skull using a frame, a portion of which is shown as a graduated element 202 in FIG. 2, and a guide tube 204 is oriented to provide the desired trajectory. The guide tube 204 has an inner lumen of sufficient diameter to receive a cannula 304. The cannula 304 is also formed as a cylinder, typically made of a metal, such as stainless steel, and has an inner lumen with a diameter sufficient to slidably receive first an inner rod (not shown) and thereafter a depth lead (the distal end 324 of a depth lead 320 is shown in FIG. 3).

The cannula 304 may be provided with a slot 306 running along its entire length so that the lead body can be extracted from the cannula without having to retract the cannula over the proximal end 330 of the lead. Thus, if the cannula 304 is slotted, the slot 306 must be dimensioned so as to allow the proximal portion of the depth lead 320 that extends proximally of the skull hole to be separated from the cannula through the slot. The depth lead 320 also has an inner lumen running through most of the length of the lead in which a stiffening element, such as a stylet, is removably disposed. (In FIG. 3, a stylet 302 is shown extending proximally of the depth lead 320). The stylet 302 may have a plastic member or stylet handle 303 at its proximal end that the surgeon can grab to more easily extract the stylet from the lead inner lumen.

One or more stop gauges may be configured so that they can encircle the proximal portion of either or both of the cannula 304 or the depth lead 320 to guard against advancing the distal end of the cannula or the depth lead beyond the target (not shown in FIG. 2 or 3). For example, the depth lead 320 may be measured in the operating room to identify a location on a proximal portion that, once the lead is being routed to the target, the surgeon can use to gauge when the lead has been advanced far enough (or to some not-to-exceed distance) into the tissue. This location on the proximal portion can be demarcated by fitting a stop gauge 310 around the lead body.

Manipulating the appropriate controls on the stereotactic equipment, the cannula 304 with the inner rod (not shown) in place is advanced into the brain. The inner rod discourages brain tissue from backing up into the cannula lumen as the cannula creates a path to the target for the lead. When the cannula 304 is advanced as far as intended, the surgeon withdraws the inner rod, and replaces it with the depth lead 320, by inserting the distal end 324 of the depth lead (with the stylet 302 in place) into the proximal end 312 (or top) of the cannula.

FIG. 3 shows a cannula 304 with a depth lead 320 inserted within the cannula inner lumen. A proximal portion 328 of the depth lead 320 extends proximally of a proximal end 312 of the cannula 304, and a distal portion 322 of the depth lead extends distally of a distal end 308 of the cannula 304. The stylet 302 is disposed in an inner lumen of the depth lead 320 and traverses substantially the full length of the depth lead 320, except for the very distal end 324 thereof. The stylet 302 is shown extending proximally of the proximal end 330 of the depth lead 320, with a stylet handle 303 at the proximal tip. The stylet 302 lends sufficient stiffness to the lead 320 while it is being manipulated during the implant procedure (e.g., to insert it into the cannula lumen. The stylet handle 303 makes it easier to remove the stylet 302 from the lead 320 before the procedure is over. It will be appreciated that in a typical stereotactic procedure, even when the depth lead 320 is inserted into the cannula 304 and after the lead distal end 324 has been delivered to the target, there is enough excess lead length so that a portion of the lead body will extend proximally of the proximal end 312 of the cannula, so that the lead at a point on the proximal portion 328 thereof can be grasped above the proximal end 312 of the cannula 304.

After the step in the procedure where the surgeon has the distal end 324 of the lead 320 where he or she wants it, the cannula 304 is removed while the lead is separated from the cannula through the slot 306. After the cannula 304 is removed, it is undesirable for subsequent steps to move the distal end 324 of the lead away from the target. But preventing that from happening can be challenging because, after the cannula 304 is removed, the stylet 302 in the inner lumen of the lead 320 still has to be extracted from the lead body before the procedure is complete. The force applied in pulling out the stylet 302 may tend to retract the distal end 324 of the lead along with it, so removing the stylet is another step which may result in dislodging the lead away from the target.

Furthermore, some form of lead fixation device typically is used to secure a proximal portion of the implanted lead at or near the skull hole or otherwise somewhere on the surface of the skull, to discourage relative movement between the implanted distal portion of the lead and the proximal portion of the lead after the procedure is complete. The step is another opportunity for unwanted displacement of the distal end of the lead from the target.

Lead Fixation Device with Compression Mechanism at Skull Hole

With reference to FIGS. 4A-9B, described are embodiments of a lead fixation device 400, 900 configured to compress against a lead body to thereby secure the lead body relative to a skull hole and prevent or at least significantly reduce movement of the lead body either further into the skull hole or out of the skull hole during implant of the lead. This lead fixation device 400, 900 secures a first portion of the lead at a skull hole where the part of the lead distal the first portion extends through the skull hole in a direction transverse to the skull surface, and secures a second portion of the lead relative to a skull surface such that the second portion rests on and along a skull surface, in a parallel arrangement with the skull surface. The lead fixation device 400, 900 overcomes the lead implanting issues described above with reference to FIGS. 2 and 3, including in particular the issues of lead movement during removal of a cannula 304 from around a lead 320 and removal of a stylet 302 from a lead.

The lead fixation device 400, 900 includes a skull attachment member 402, 902 configured to be secured to the skull and a flexible compression mechanism 406, 906 that is associated with the skull attachment member. The compression mechanism 406, 906 is configured to compress radially outward to expand its inner diameter to receive a lead implant tool, e.g., a cannula, and then expand radially inward to reduce its inner diameter to compress against a portion of the lead body upon removal of the lead implant tool.

With continued reference to FIGS. 4A-9B, the skull attachment member 402, 902 includes a central bore 410, 910 and lead securing features corresponding to surface channels 414, 914 formed in the body 415, 915 of the of the attachment member and that extend from the central bore to the outer perimeter 417, 917 of the attachment member. The skull attachment member 402, 902 may also include a pair of opposed protrusions 416, 916 at a location along the length of each of the surface channels 414, 914. These protrusions 416, 916 extend inward toward the center 419, 919 of the channel 414, 914 to provide an area of reduced width of the channel that functions to secure a portion of a lead body in place in the channel. The skull attachment member 402 also includes a pair of screw holes 412, 912 for receiving bone screws 408, 908 that secure the lead fixation device 400, 900 to the skull. The bone screws 408, 908 may be preinstalled into the screw holes 412, 912 via an interference fit, or they may be separately installed through the holes after placement of the skull attachment member 402, 902.

With reference to FIGS. 6-8B, the compression mechanism 406 is located in a first recess 418 formed in the skull attachment member 402 that surrounds the central bore 410, and is secured in place by a locking ring 404 that fits in a second recess 420 that also surrounds the central bore. The skull attachment member 402 and the locking ring 404 are formed of a rigid plastic, e.g., PEEK. The locking ring 404 includes a circular recess 430 sized to receive the compression mechanism 406. The diameter 432 of the recess 430 is slightly greater than the outer diameter 426 of the compression mechanism to provide a space for radial expansion of the compression mechanism and a corresponding increase in the size of its inner diameter 424 when a cannula is inserted through the opening defined by the compression mechanism.

The compression mechanism 406 is formed of a flexible material, e.g., silicone, and is configured such that the inner diameter 424 defined by the compression mechanism expands to accommodate insertion of a cannula 304 and contracts to fit tightly around a lead body (when the cannula is removed from the compression mechanism) to prevent movement of the lead relative to a skull hole. Properties of the compression mechanism, including the inner diameter 424, the outer diameter 426 and the cross-section diameter 428, and the stiffness of the compression mechanism material may be selected to obtain the desired results.

While the compression mechanism 406, 906 in the embodiments in FIGS. 4A-9B is in the form of an O-ring, other types of compression mechanisms are contemplated. For example, the compression mechanism may be defined by a slot with silicone on each side that defines a cross-section width that compresses a portion of a lead body sufficiently to secure the lead in place in relative to a skull hole.

With reference to FIGS. 10A-10J, an example implant procedure for the lead fixation device 400 of FIGS. 4A-8B is provided. A twist drill hole 440 is formed in a location of the cranium 444 using known stereotactic techniques. (See FIG. 10A.) The distal end of a split (or slotted) cannula 304 (with an inner rod 446 inserted) is slid through a passageway or bore 410 of the lead fixation device 400 that is defined by a compression mechanism 406 of the device. The size of the passageway, which is defined by an expanded inner diameter 424 of the compression mechanism 406, exerts sufficient radial pressure on the cannula 304 to hold the lead fixation device 400 in place on the cannula. (See FIG. 10B.)

The distal portion of slotted cannula 304 (with the inner rod 446 inserted) it is inserted through the twist drill hole 440, into the brain to a known depth using stereotactic techniques. (See FIG. 10C.) The lead fixation device 400 is slid down the cannula 304 in direction A (see FIG. 10c) to rest on top of the cranium 444 and is secured in place using bone screws 408. (See FIG. 10D.)

The inner rod 446 in the cannula 304 is removed by pulling on the inner rod 446 in direction B. (See FIG. 10E.) The lead 320 with a stylet 302 inserted is inserted into the cannula 304 and advanced in direction C to the known/ predetermined depth using known stereotactic techniques. (See FIG. 10F.)

The cannula 304 is removed from around the lead 320 through the slot 306 of the cannula. (See FIG. 10G.) Or, in other words, the lead 320 is separated from the cannula 304 through the slot 306. When the cannula 304 is removed, the size of the passageway of the lead fixation device 400, which is defined by a slightly less expanded inner diameter 424 of the compression mechanism 406, shrinks into abutting contact with a portion of the lead 320 and applies enough inward force on the lead to secure the lead in place at the twist drill hole 440 so the lead is not displaced in either distal or proximal direction.

The stylet 302 inserted in the lead 320 is removed from the lead in direction D. (See FIG. 10H.) The lead 320 is left secure in place by the compression mechanism 406 and a proximal portion 328 of the lead 320 is available for routing to a neurostimulator can. (See FIG. 10I.) A second portion 450 of the lead 320 is locked in place in a channel 414 of the lead fixation device 400 and routed along the surface of the cranium 444 to a neurostimulator can; and bone screws 408 are then used to secure the lead fixation device 400 to the surface of the cranium 444. (See FIG. 10J.)

Thus disclosed is a lead fixation device 400, 900 for securing a first portion 448 of a lead 320 relative to a hole 440 formed through a skull. The lead fixation device 400 includes a skull attachment member 402, 902 having an upper surface 421 and a lower surface 423 and a bore 410, 910 extending through and between the upper surface and the lower surface. The lead fixation device 400, 900 also includes a lead compression mechanism 406, 906 that is integral with the skull attachment member 402, 902 and aligned with the bore 410, 910 of the skull attachment member. Integral in this context means the lead fixation device 400, 900 is formed of components assembled into a single assembly that cannot be disassembled without damaging the structural integrity of one or more of the component parts.

The lead compression mechanism 406, 906 defines or forms a passageway 425, 925 through the lead fixation device 400, 900, which passageway is characterized by a diameter 424, 924 that is defined by the lead compression mechanism. The lead compression mechanism 406, 906 is configured to transition the diameter 424, 924 from a first size to a second size greater than the first size upon insertion of an implant tool 304 through the passageway 425, 925, and from the second size to the first size upon removal of the implant tool from the passageway.

In one configuration, the compression mechanism 406, 906 is fixedly secure relative to the skull attachment member 402, 902 so that transition of the diameter 424, 924 between the first size and the second size results from radial outward compression of the compression mechanism and radial inward expansion of the compression mechanism relative to an axis 427, 927 through the passageway 425, 925. The first portion 448 of the lead 320 has a diameter and the first size of the diameter 424, 924 of the compression mechanism 406, 906 is less than the diameter of the lead to thereby secure the first portion of the lead in place at the hole 440.

Thus, the functionality of the lead fixation device 400, 900 is imparted by compression and expansion of the compression mechanism and no displacement or movement of the compression mechanism up or down along the axis, or about the axis is required. In fact, no relative movement between the components of the lead fixation device 400, 900 occurs when securing a lead in place—other than compression and expansion of the compression mechanism within the skull attachment member. This is distinct from prior art burr hole fixation devices where movement of one part, e.g., a lid or cap, relative to another part, e.g. a base, is required to secure a lead in place.

The compression mechanism 406, 906 is formed of a flexible material, e.g., silicone, that compresses from a normal state upon receipt of force by the implant tool 304 and returns to the normal state in an absence of such force. In one configuration, the lead compression mechanism is an O-ring. In another configuration, the lead compression mechanism is formed by a pair of structures on opposite sides of the bore 410, 910 of the skull attachment member.

The skull attachment member 402, 902 is formed of a material more rigid than the lead compression mechanism. The skull attachment member 402, 902 also includes at least one surface channel 414, 914 configured to receive a second portion 450 of the lead proximal the first portion of the lead.

Lead Fixation Devices with Compression Mechanism Along Skull Surface

Figure 11:
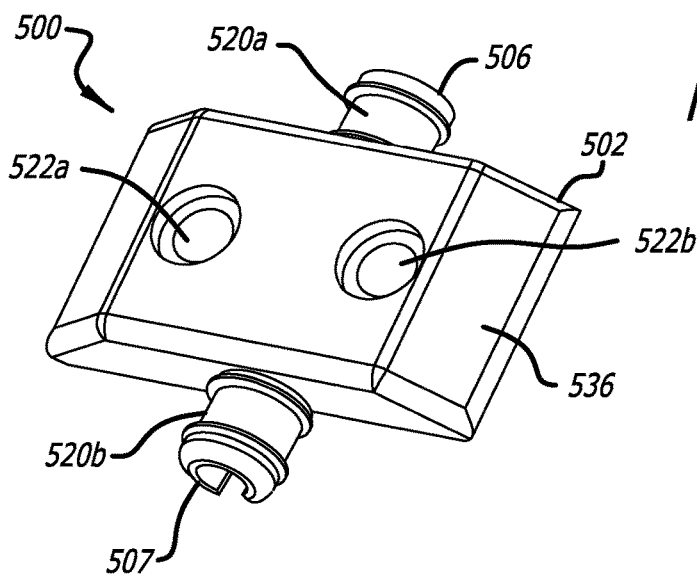
FIGS. 11 and 12 are illustrations of a first embodiment of a lead fixation device for securing a lead on a surface of the skull.
Figure 12:
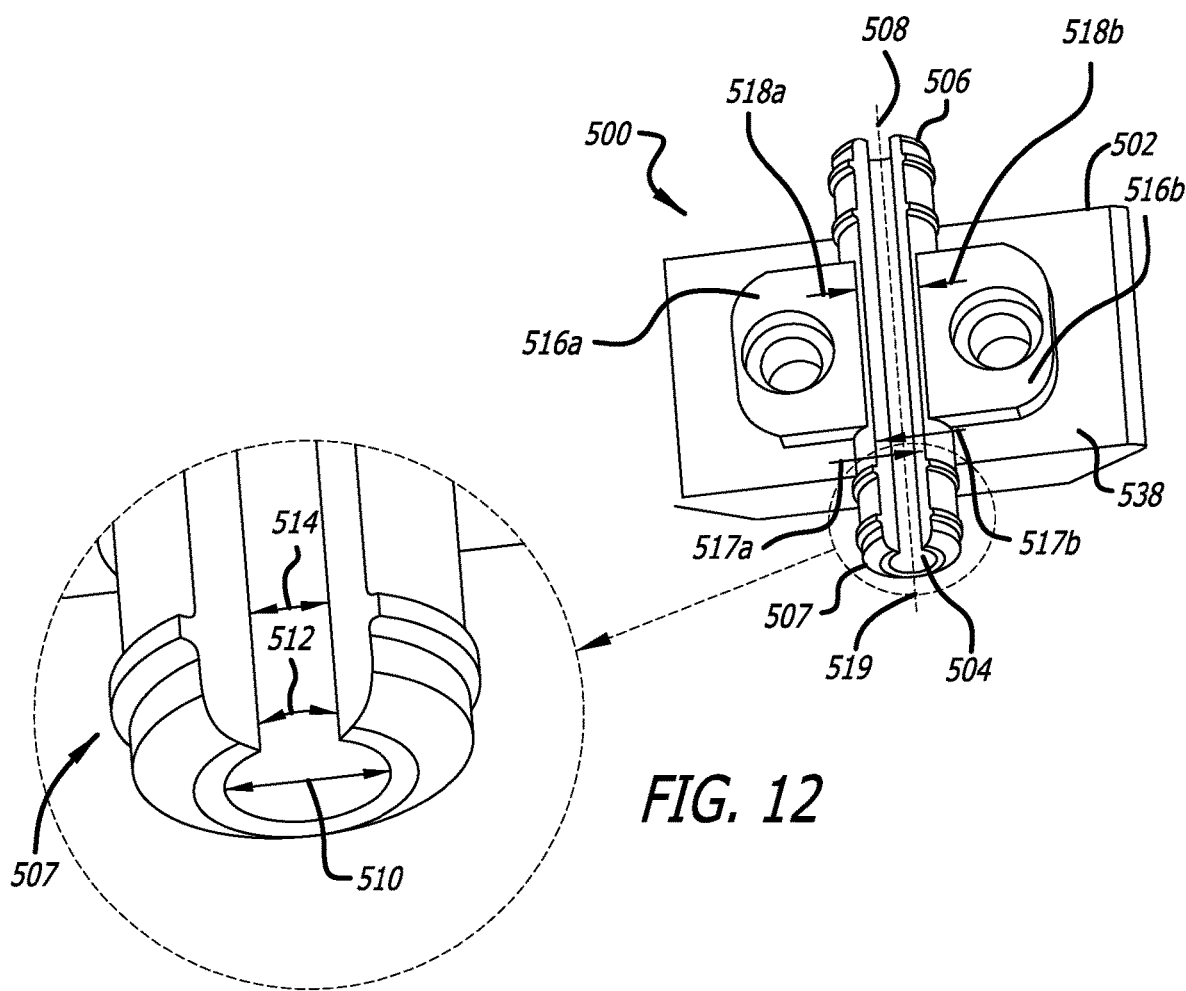

With reference to FIGS. 11 and 12, described is a first embodiment of a lead fixation device 500 configured to compress against a lead body to thereby secure the lead body relative to a skull surface adjacent a skull hole. The lead fixation device 500 prevents or at least significantly reduces movement of the lead body either further into the skull hole or out of the skull hole during implant of the lead. This lead fixation device 500 secures a portion of the lead relative to a skull surface such that the portion rests on and along a skull surface, in a parallel arrangement with the skull surface.

The lead fixation device 500 includes a skull attachment member 502 configured to be secured to the skull and a flexible compression mechanism 506 that is associated with the skull attachment member. The compression mechanism 506 is configured to receive a portion of a lead body through a slot 508 and then to compress against the portion of the lead body upon receipt of a compressive force.

The skull attachment member 502 is formed of a rigid plastic, e.g., PEEK. The compression mechanism 506 is formed of a material, e.g., silicone, that is softer and more flexible than the material of the skull attachment member. During production of the lead fixation device 500, the skull attachment member 502 may be formed first with the compression mechanism 506 being formed over and within recesses of the skull attachment member to produce an integral, single piece structure with no moving parts. Integral in this context means the lead fixation device 500 is formed of components assembled into a single assembly that cannot be disassembled without damaging the structural integrity of one or more of the component parts.

With reference to FIG. 12, the compression mechanism 506 defines a passageway 504 through the skull attachment member 502. The passageway 504 is provided by a c-shaped tube 507 having a slot 508 that extends along the length of the tube. The c-shaped tube 507 is characterized by an inner diameter 510 that is sized to receive a portion of a lead body. In one configuration, the slot 508 is characterized by an inner arc 512 that extends between 25-35 degrees around the circumference of the inside of the c-shaped tube 507. As such, the width 514 of the slot 508 is less than the inner diameter 510 of the tube 507.

The flexibility of the c-shaped tube 507, however, allows for the portions of the tube adjacent the slot 508 to deform upon receipt of first forces 517a, 517b in the direction away from the axis 519 of the tube 507 and further separate from each to thereby allow a lead body to fit through the slot 508 to the interior of the tube. Once the lead body is in the interior of the c-shaped tube 507 and the first forces 517a, 517b are removed, the deformed portions of the tube adjacent the slot 508 return to their pre-deformed state and the c-shaped tube assumes its normal shape to secure the lead body within the interior of the tube. In other configurations, the size of the inner arc 512 and the resulting slot 508 may be greater than or equal to the inner diameter 510 of the tube 507.

With continued reference to FIG. 12, in one configuration the compression mechanism 506 includes a pair of wings 516a, 516b that extend outward from a portion of the c-shaped tube 507 in opposite directions. These wings 516a, 516b are formed of the same flexible material as the c-shaped tube 507 and have a thickness of about 0.5 mm. When the lead fixation device 500 is secured to the skull by bone screws, the flexibility of the pair of wings 516a, 516b allows them to flatten somewhat under the force of compression resulting from the screwing down of the skull attachment member 502. This flattening translates into a receipt of second forces 518a, 518b in the direction toward the axis 519 of the tube 507. These second forces 518a, 518b cause the width 514 of the slot 508 in the area of the wings 516a, 516b to reduce, which serves to further secure the lead in place and prevent movement of the lead body in either direction along the length of the tube 507. Compression of the silicone c-shaped tube 507 itself along the length of the tube may also serve to secure the lead in place.

With reference to FIG. 11, the compression mechanism 506 may also include a pair of circumferential grooves 520a, 520b configured to secure a suture in place around the c-shaped tube 507. Sutures may thus be applied at either end of the c-shaped tube to further secure the lead body in place. However, given the above described functionality of the wings 516a, 516b, the use of sutures is optional as the second forces 518a, 518b imparted by the wings by the securing of the device to the skull is sufficient to secure the lead in place and prevent movement of the lead body in either direction along the length of the compression mechanism 506.

With continued reference to FIG. 11, the skull attachment member 502 includes a pair of screw holes 522a, 522b configured to receive a bone screw. The skull attachment member 502 has a maximum thickness of 2 mm in the region of the screw holes and tapers downward to a reduced thickness at the side edges.

Figure 13:
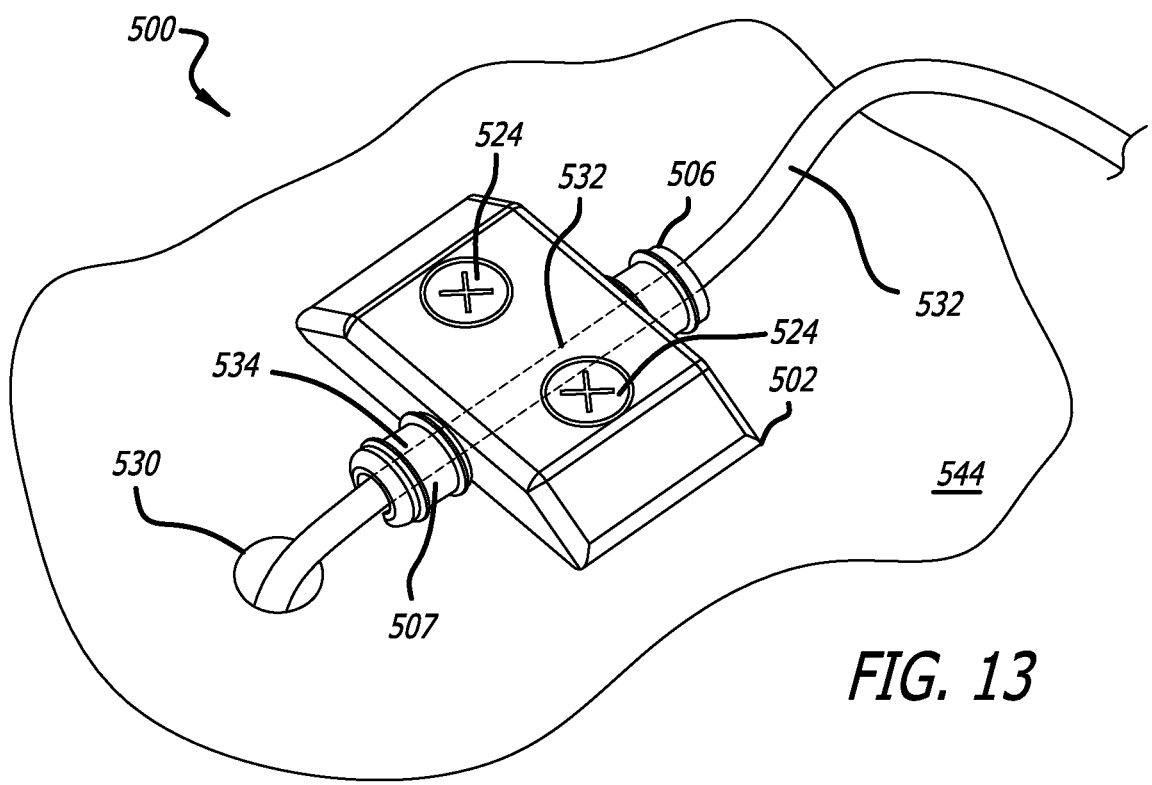
FIG. 13 is an illustration of a lead implant procedure using the lead fixation device of FIGS. 11 and 12.

With reference to FIG. 13, an example implant procedure for the lead fixation device of FIGS. 11 and 12 is provided. A twist drill hole 530 is formed in location of the cranium using known stereotactic techniques. A lead 532 is implanted using known techniques.

The passageway 504 of the compression mechanism 506, as defined by a c-shaped tube 507, is aligned with the body of the lead 532 and a portion of the lead body is pushed through the slot 508 into the passageway of the c-shaped tube. The lower surface 538 of the skull attachment member 502 is positioned relative to the skull surface to place the wings 516a, 516b of the compression mechanism 506 on the skull surface.

The lead fixation device 500 is secured to the surface 544 skull using bone screws 524. The screws are advanced into the bone to a level sufficient to cause the pair of wings 516a, 516b to flatted and apply second forces 518a, 518b that cause the width 514 of the slot 508 in the area of the wings 516a, 516b to reduce, which serves to secure the lead in place and prevent movement of the lead body in either direction along the length of the tube.

Thus disclosed is a lead fixation device 500 for securing a portion 534 of a lead 532 relative to a surface 544 of a skull. The lead fixation device 500 includes a skull attachment member 502 having an upper surface 536 and a lower surface 538. The lead fixation device 500 also includes a lead compression mechanism 506 that is integral with the skull attachment member 502. Integral in this context means the lead fixation device 500 is formed of components assembled into a single assembly that cannot be disassembled without damaging the structural integrity of one or more of the component parts. The lead compression mechanism 506 is formed of a flexible material, e.g., silicone, while the skull attachment member 502 is formed of a material more rigid than the lead compression mechanism, such as PEEK.

The lead compression mechanism 506 forms a passageway 504 through the skull attachment member 502. The passageway 504 is characterized by a slot 508 that faces in the direction of the lower surface 538 and extends along the length of the passageway.

The lead compression mechanism 506 is formed of a flexible material, e.g., silicone, and is configured to transition a width 514 of the slot 508 from an initial size that is less than the diameter of the portion 534 of the lead 532, to an expanded size that is greater than the initial size upon receipt of appropriately directed first forces 517a, 517b in a region of the lead compression mechanism 506 that forms the passageway 504. These first forces 517a, 517b may be respectively applied against a facing edge of the c-shaped tube 507 in opposite direction relative to the axis 519 of the passageway 504. As such, the first forces 517a, 517b increase the width 514 and allow for the portion 534 of the lead 532 to slide into the passageway 504.

The lead compression mechanism 506 is further configured to transition the width 514 of the slot 508 from the initial size to a collapsed size upon receipt of appropriately directed second force 518a, 518b in a region of the lead compression mechanism 506 that forms the passageway 504. These second forces 518a, 518b may be respectively applied along an outer surface of the c-shaped tube 507 toward each other. As such, the second forces 518a, 518b decrease the width 514 and secure the portion 534 of the lead 532 inside the passageway 504. In one configuration, the lead compression mechanism 506 includes at least one wing 516a, 516b that extends to a side of the passageway 504 and along the lower surface 538 of the skull attachment member 502. These wings 516a, 516b function to distribute the second forces 518a, 518b along the c-shaped tube 507.

Figure 14:
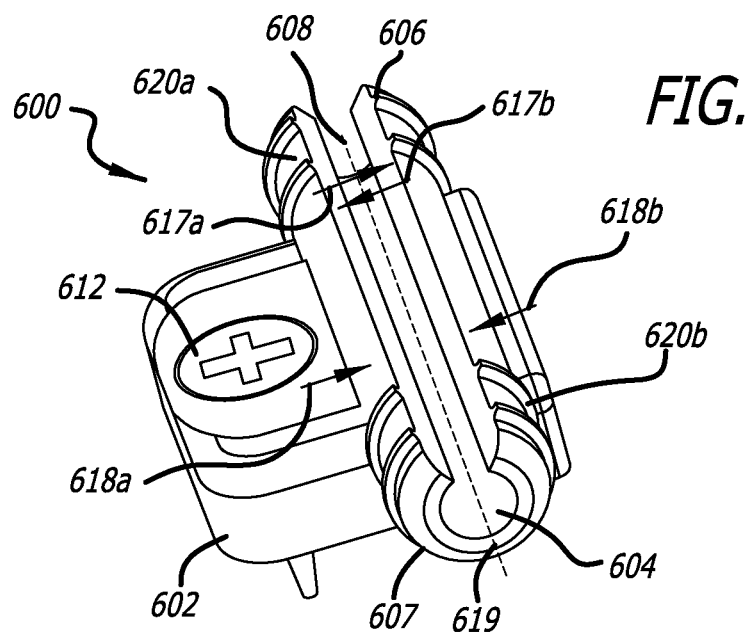
FIGS. 14, 15A, and 15B are illustrations of a second embodiment of a lead fixation device for securing a lead on a surface of the skull.
Figure 15A:
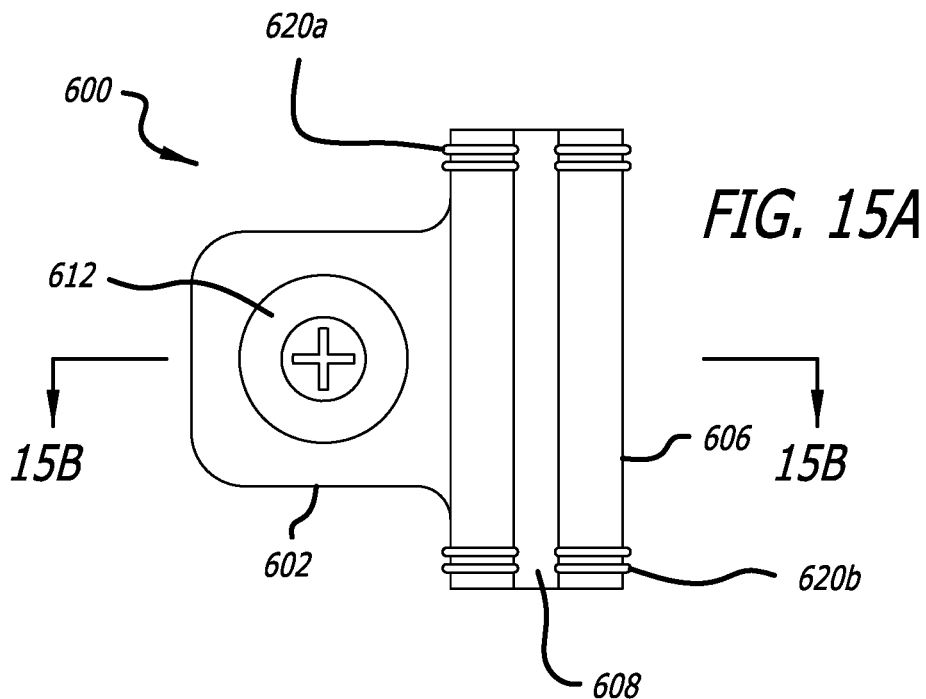
Figure 15B:
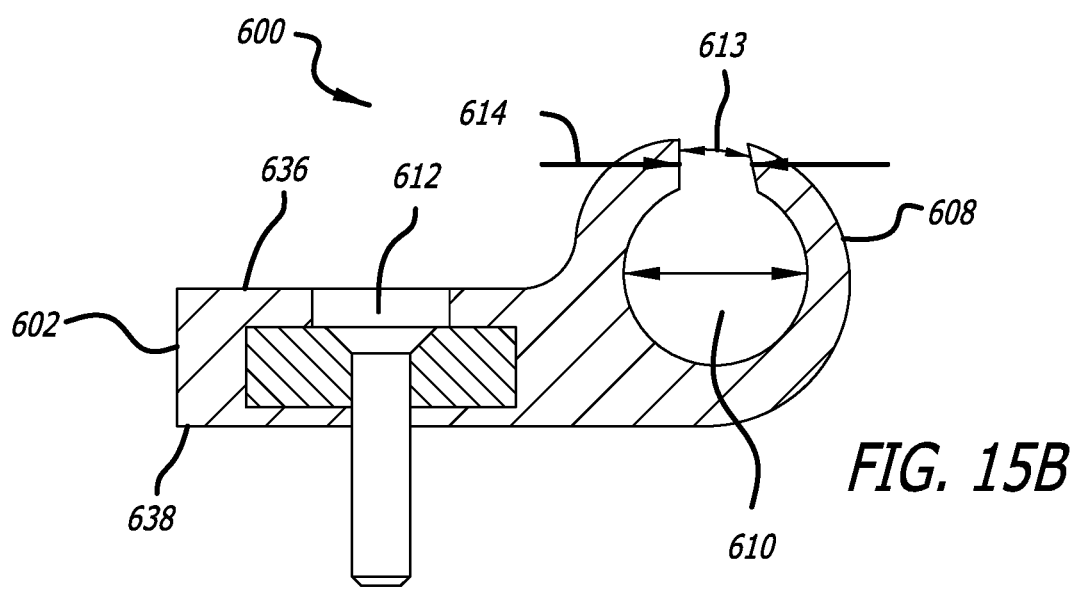

With reference to FIGS. 14, 15A, and 15B, described is a second embodiment of a lead fixation device 600 configured to compress against a lead body to thereby secure the lead body relative to a skull surface adjacent a skull hole and prevent or at least significantly reduce movement of the lead body either further into the skull hole or out of the skull hole during implant of the lead. This lead fixation device 600, like the fixation device 500 described above with reference to FIGS. 11 and 12, secures a portion of the lead relative to a skull surface such that the portion rests on and along a skull surface, in a parallel arrangement with the skull surface.

The lead fixation device 600 includes a skull attachment member 602 configured to be secured to the skull and a flexible compression mechanism 606 that is associated with the skull attachment member. The compression mechanism 606 is configured to receive a portion of a lead body through a slot 608 and then to compress against the portion of the lead body upon receipt of a compressive force.

The skull attachment member 602 is formed of a rigid plastic, e.g., PEEK. The compression mechanism 606 is formed of a material, e.g., silicone, that is softer and more flexible than the material of the skull attachment member. During production of the lead fixation device 600, the skull attachment member 602 may be formed first, with the compression mechanism 606 being formed over and within recesses of the skull attachment member to produce an integral, single-piece structure. Integral in this context means the lead fixation device 600 is formed of components assembled into a single assembly that cannot be disassembled without damaging the structural integrity of one or more of the component parts.

With reference to FIG. 14, the compression mechanism 606 defines a passageway 604 through the skull attachment member 602. The passageway 604 is provided by a c-shaped tube 607 having a slot 608 that extends along the length of the tube. The c-shaped tube 607 is configured the same as the c-shaped tube 507 described above with reference to FIGS. 11 and 12. Thus, the c-shaped tube 607 is characterized by an inner diameter 610 that is sized to receive a lead body. The slot 608 is characterized by an inner arc 613 that extends between 25-35 degrees around the circumference of the inside of the c-shaped tube 607. As such, the width 614 of the slot 608 is less than the inner diameter of the tube 607.

The flexibility of the c-shaped tube 607, however, allows for the portions of the tube adjacent the slot 608 to deform upon receipt of first forces 617a, 617b and further separate from each to thereby allow a portion of a lead body to fit through the slot to the interior of the tube. Once the portion of the lead body is within the interior of the c-shaped tube 607 and the first forces 617a, 617b are removed, the deformed portions of the tube adjacent the slot 608 return to their pre-deformed state and the c-shaped tube assumes its normal shape to secure the lead body within the interior of the tube.

The compression mechanism 606 may also include a pair of circumferential grooves 620a, 620b configured to secure a suture in place around the c-shaped tube 607. Sutures may thus be applied at either end of the c-shaped tube 607 to further secure the lead body in place and prevent movement of the lead body in either direction along the length of the tube. The skull attachment member 602 includes a screw hole configured to receive a bone screw 612.

Figure 16A:
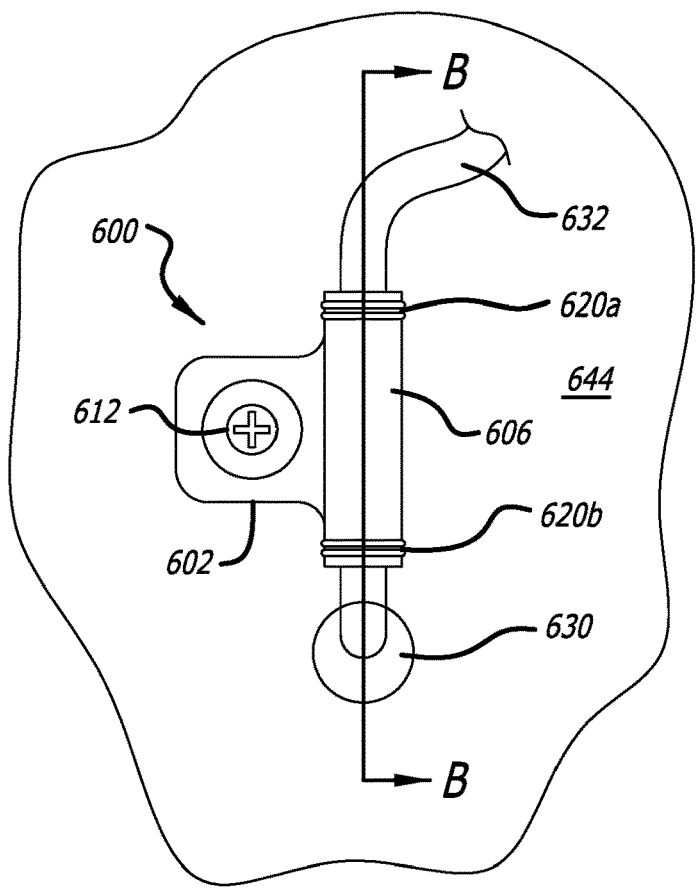
FIGS. 16A and 16B are illustrations of a lead implant procedure using the lead fixation device of FIG. 14.
Figure 16B:
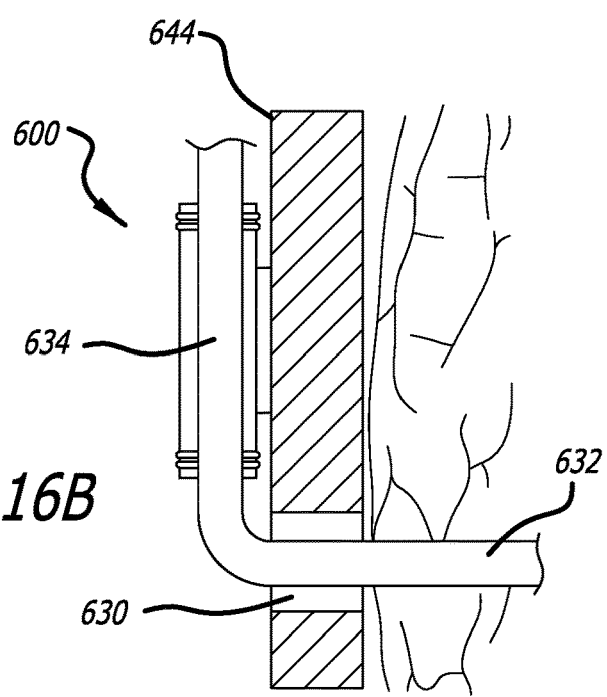

With reference to FIGS. 16A and 16B, an example implant procedure for the lead fixation device of FIGS. 14, 15A, and 15B is provided. A twist drill hole 630 is formed in location of the cranium 644 using known stereotactic techniques. A lead 632 is implanted using known techniques such that a portion of the lead passes through the twist drill hole 630 and is beneath the cranium 644 in the brain, and a portion of the lead rests on top of the cranium.

The compression mechanism 606 of a lead fixation device 600 is aligned with the body of the lead 632 and a portion 634 of the lead body is pushed through the slot 608 into the compression mechanism. The skull attachment member 602 of the lead fixation device 600 is positioned relative to the surface of the cranium 644 and is secured to the skull using a bone screw 612. Sutures are secured around the pair of circumferential grooves 620a, 620b to secure the portion 634 of the lead 632 body in place in the compression mechanism 606 and prevent movement of the lead body in either direction along the length of the compression mechanism.

Thus disclosed is a lead fixation device 600 for securing a portion 634 of a lead 632 relative to a surface of a skull or cranium 644. The lead fixation device 600 includes a skull attachment member 602 having an upper surface 636 and a lower surface 638. The lead fixation device 600 also includes a lead compression mechanism 606 that is integral with the skull attachment member 602. Integral in this context means the lead fixation device 600 is formed of components assembled into a single assembly that cannot be disassembled without damaging the structural integrity of one or more of the component parts. The lead compression mechanism 606 is formed of a flexible material, e.g., silicone, while the skull attachment member 602 is formed of a material more rigid than the lead compression mechanism, such as PEEK.

The lead compression mechanism 606 forms a passageway 604 through the skull attachment member 602. The passageway 604 is characterized by a slot 608 that faces in the direction of the upper surface 636 and extends along the length of the passageway.

The lead compression mechanism 606 is formed of a flexible material, e.g., silicone, and is configured to transition a width 614 of the slot 608 from an initial size that is less than the diameter of the portion 634 of the lead 632, to an expanded size that is greater than the initial size upon receipt of appropriately directed first forces 617a, 617b in a region of the lead compression mechanism 606 that forms the passageway 604. These first forces 617a, 617b may be respectively applied against a facing edge of the c-shaped tube 607 in opposite direction relative to the axis 619 of the passageway 604. As such, the first forces 617a, 617b increase the width 614 and allow for the portion 634 of the lead 632 to slide into the passageway 604.

The lead compression mechanism 606 is further configured to transition the width 614 of the slot 608 from the initial size to a collapsed size upon receipt of appropriately directed second force 618a, 618b in a region of the lead compression mechanism 606 that forms the passageway 604. These second forces 618a, 618b may be respectively applied along an outer surface of the c-shaped tube 607 toward each other. As such, the second forces 618a, 618b decrease the width 614 and secure the portion 634 of the lead 632 inside the passageway 604. The second forces 618a, 618b may result from the placement and tying of a suture in each of the grooves 620a, 620b.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A lead fixation device for securing a portion of a lead relative to a surface of a skull, the lead fixation device comprising:

a skull attachment member having an upper surface and a lower surface; and a compression mechanism integral with the skull attachment member and forming a passageway relative to the skull attachment member, which passageway is characterized by a slot that extends along a length of the passageway, wherein the compression mechanism is configured to:
   transition a width of the slot from an initial size to an expanded size that is greater than the initial size upon a receipt of appropriately directed first forces in a region of the compression mechanism that forms the passageway, and
   transition the width of the slot from the initial size to a collapsed size upon a receipt of appropriately directed second forces in a region of the compression mechanism that forms the passageway.

2. The lead fixation device of claim 1, wherein the compression mechanism is formed of a flexible material.

3. The lead fixation device of claim 1, wherein the portion of the lead has a diameter, and the initial size is less than the diameter and the expanded size is greater than the diameter.

4. The lead fixation device of claim 1, wherein the skull attachment member is formed of a material more rigid than the compression mechanism.

5. The lead fixation device of claim 1, wherein the slot faces in the direction of the lower surface of the skull attachment member.

6. A lead fixation device for securing a portion of a lead relative to a surface of a skull, the lead fixation device comprising:

a skull attachment member having an upper surface and a lower surface; and a compression mechanism integral with the skull attachment member and forming a passageway relative to the skull attachment member, which passageway is characterized by a slot that extends along a length of the passageway and faces in the direction of the lower surface of the skull attachment member, wherein the compression mechanism comprises at least one wing extending to a side of the passageway and along the lower surface of the skull attachment member and is configured to:
   transition a width of the slot from an initial size to an expanded size that is greater than the initial size upon a receipt of appropriately directed first forces in a region of the compression mechanism that forms the passageway, and
   transition the width of the slot from the initial size to a collapsed size upon a receipt of appropriately directed second forces in a region of the compression mechanism that forms the passageway.

7. The lead fixation device of claim 1, wherein the slot faces in the direction of the upper surface of the skull attachment member.

8. The lead fixation device of claim 1, wherein the passageway extends along the upper surface of the skull attachment member.

9. The lead fixation device of claim 1, wherein the passageway extends along the lower surface of the skull attachment member.

* * * * *